United States Patent [19]
Leistner et al.

[11] Patent Number: 4,460,725
[45] Date of Patent: Jul. 17, 1984

[54] POLYETHERS CONTAINING 2,2,6,6-TETRAMETHYL PIPERIDINYL CARBOXYLIC ACID ESTER GROUPS AND SYNTHETIC RESIN COMPOSITIONS

[76] Inventors: William E. Leistner, 1458 Bay Blvd., Atlantic Beach, N.Y. 11509; Motonobu Minagawa, 1-207-3 Shichizacho, Koshigaya City, Saitama, Japan; Naohiro Kubota, 3-105 Ageo Higashi Danchi, 404-1 Ageo-mura, Ageo City, Saitama, Japan; Toshihiro Shibata, 136-49-3-104 Nara-cho, Omiya City, Saitama, Japan; Ryozo Arata, 418-1 Shikatebukuro, Urawa City, Saitama, Japan

[21] Appl. No.: 472,710

[22] Filed: Mar. 7, 1983

[30] Foreign Application Priority Data

Mar. 8, 1982 [JP] Japan ................................. 57-36312

[51] Int. Cl.$^3$ ...................... C08K 5/34; C07D 403/00; C07D 251/00; C07D 251/28
[52] U.S. Cl. .................................. 524/102; 546/188; 546/189; 546/190; 546/191; 546/209
[58] Field of Search ................ 524/102; 546/188, 189, 546/190, 191, 209; 525/113

[56] References Cited

U.S. PATENT DOCUMENTS 3,998,784 12/1976 Cook ................................... 524/102
4,212,974 7/1980 Murayama et al. .................. 523/456
4,256,627 3/1981 Moser et al. ......................... 524/100
4,336,183 6/1982 Nakahara et al. .................... 524/99

Primary Examiner—Morton Foelak
Assistant Examiner—Kriellion Morgan

[57] ABSTRACT

Polyethers containing 2,2,6,6-tetramethyl piperidinyl carboxylic acid ester or ether groups are provided, comprising polymeric units having the structure

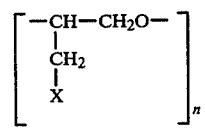

wherein
X is selected from the group consisting of:

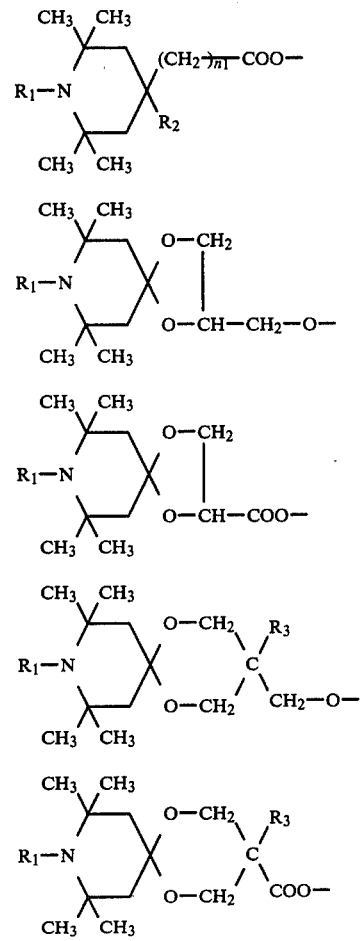

$R_1$ is selected from the group consisting of hydrogen, —O, alkyl, hydroxy alkyl and epoxyalkyl having from one to about eighteen carbon atoms, acyl having from one to about eighteen carbon atoms, cycloalkyl having from three to about eighteen carbon atoms; phenyl; phenalkyl and alkylphenyl having from seven to about twenty-four carbon atoms;
$R_2$ is hydrogen or hydroxy;
$n_1$ is 0 or 1;
$R_3$ is lower alkyl having from one to about six carbon atoms; and
n is the average number of such units in the polymer; as well as stabilized synthetic resin compositions comprising such polyethers.

25 Claims, No Drawings

POLYETHERS CONTAINING 2,2,6,6-TETRAMETHYL PIPERIDINYL CARBOXYLIC ACID ESTER GROUPS AND SYNTHETIC RESIN COMPOSITIONS

Polymers such as polyethylene, polypropylene, ABS resin, polyvinyl chloride and polyurethane undergo degradation and discoloration when subjected to irradiation by ultraviolet light such as sunlight, with deterioration in mechanical strength. Accordingly, various kinds of light stabilizers have been incorporated in such polymers to lessen their deterioration. However, the available stabilizers are unsatisfactory in their stabilizing effectiveness, unstable to heat and oxidation, and soluble in water or organic solvents. Some stabilizers even impart a color of their own to the polymers.

2,2,6,6-tetramethyl piperidine compounds do not impart color to the polymer, and act as quenchers. Many piperidine compounds, therefore, are proposed as light stabilizers.

Cook U.S. Pat. No. 3,998,784, patented Dec. 21, 1976, provides compounds having the formula:

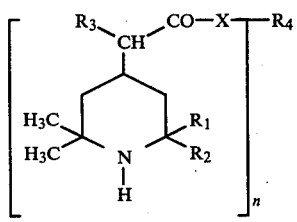

wherein $R_1$ and $R_2$ are the same or different and each is a straight- or branched alkyl residue having from 1 to 12 carbon atoms, or $R_1$ and $R_2$, together with the carbon atom to which they are attached form a cycloalkyl group having from 5 to 12 carbon atoms; $R_3$ is hydrogen, a straight- or branched alkyl residue having from 1 to 4 carbon atoms, an aralkyl residue having from 7 to 9 carbon atoms or a cycloalkyl group having 5 or 6 carbon atoms; $R_4$ is a metal ion or a hydrocarbyl residue having from 2 to 20 carbon atoms and being either unsubstituted or substituted by halogen or interrupted by one or more oxygen or sulphur atoms, X is —O—, —S—, or >$NR_5$, wherein $R_5$ has the same significance as $R_3$; and n is 2, 3 or 4; as well as salts of the amine function of the compounds of formula I.

When n is 2, $R_4$ may be a divalent, straight- or branched aliphatic residue (either saturated or unsaturated) having from 2 to 20 carbon atoms, a divalent alicyclic residue having from 5 to 20 carbon atoms, a divalent aralkyl residue having 8 to 20 carbon atoms, or a divalent aryl residue having 6 to 20 carbon atoms.

When n is 3, $R_4$ may be a trivalent straight- or branched chain aliphatic (either saturated or unsaturated) residue having 3 to 15 carbon atoms, a trivalent alicyclic residue having 5 to 15 carbon atoms, a trivalent aralkyl residue having from 9 to 15 carbon atoms, or a trivalent aryl residue having 6 to 16 carbon atoms.

When n is 4, $R_4$ may be a straight- or branched chain tetravalent aliphatic residue (either saturated or unsaturated) having 4 to 12 carbon atoms or a tetravelent alicyclic residue having from 5 to 12 carbon atoms, such as tetramethylenemethane or 1,1,4,4-tetramethylene cyclohexane.

When n is 2, 3 or 4 and $R_4$ is an aliphatic or alicyclic residue each of these residues may be unsubstituted or substituted by halogen or interrupted by one or more oxygen or sulphur atoms or an aryl or aralykyl residue.

Hillard et al U.S. Pat. No. 4,064,102, patented Dec. 20, 1977, provides compounds of the formula:

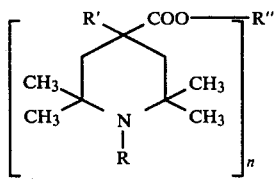

wherein R is hydrogen or alkyl ($C_1$–$C_8$), R' is hydrogen, hydroxyl or lower alkoxy ($C_1$–$C_8$); R" is alkyl ($C_1$–$C_{20}$), alkylene ($C_2$–$C_{12}$), cycloalkyl, wherein the alicyclic ring contains 5- or 6-carbon atoms, cycloalkylene, wherein the alicyclic ring may contain lower alkyl substituents, alkenyl ($C_3$–$C_{20}$), arylene or aralkylene; n is an integer from 1 to 4, useful for stabilizing polyolefin polymers against photo and thermal degradation.

Murayama et al U.S. Pat. No. 4,212,974, patented July 15, 1980, provides piperidine derivatives having the formula:

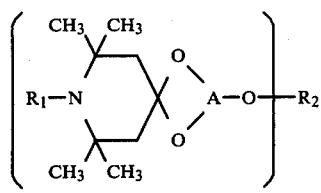

wherein $R_1$ represents hydrogen, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, n is an integer of 1 to 4; when n is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, a N-substituted carbamoyl group, a N-substituted thiocarbamoyl group, a monovalent group from an oxoacid or group

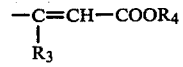

in which $R_3$ represents hydrogen atom, a lower alkyl group or phenyl group and $R_4$ represents an alkyl group; when n is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid; when n is 3, $R_2$ represents an aromatic triacyl group or a trivalent group from an oxoacid; and when n is 4, $R_2$ represents an aromatic tetraacyl group, and A represents a group

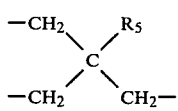

in which $R_5$ represents hydrogen atom or a lower alkyl group or, when n is 1, $R_5$ may represent together with $R_2$ a group

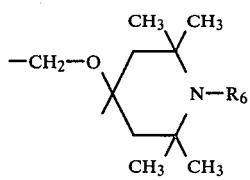

in which $R_6$ represents the same group as defined in $R_1$ and may be the same or different from $R_1$, or a group

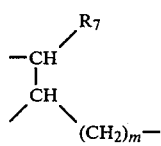

in which n is 1 or 2 and $R_7$ represents hydrogen atom or, when n and m are 1, $R_7$ represents methylene group together with $R_2$.

These piperidine derivatives have a stabilizing effect against photo- and thermal-deterioration of synthetic polymeric materials such as polyolefin, polyvinyl chloride, polyvinylidene chloride, polyacetal, polyester, polyamide, polyurethane, epoxy resins and the like.

Rody et al U.S. Pat. No. 4,234,699, patented Nov. 18, 1980, provides condensation polymers and addition polymers having as the recurrent molecular unit a polyalkylpiperidine radical of the formula or having a polyalkylpiperidine side group of the formula

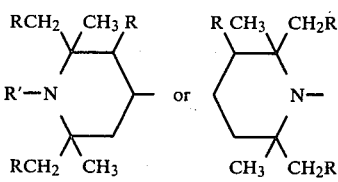

in which R denotes hydrogen or alkyl with 1–5 C atoms and R' denotes hydrogen, alkyl with 1–12 C atoms alkenyl with 3–8 C atoms, alkinyl with 3–6 C atoms, aralkyl with 7–12 C atoms, alkanoyl with 1–8 C atoms or alkenoyl with 3–5 C atoms, and copolymers with one another or with polyalkylpiperidine-free components.

Condensation polymers and addition polymers are to be understood as those polymers or oligomers which are manufactured by a polycondensation reaction or polyaddition reaction and possess hetero-atoms in the polymer chain. Examples of such polymers are polyesters, polyethers, polyamides, polyamines, polyurethanes, polyureas, polysulphides, polysulphones, polyimides, polysulphonates, polyphosphates, polyphosphonates, polysilyl esters, polysiloxanes, polyhydrazides, polyhydrazones or polybenzimidazoles.

Nakahara et al U.S. Pat. No. 4,336,183, patented June 22, 1982, provides 2,2,6,6-tetramethyl-4-piperidyl carboxylic acid esters and amides of mono and poly alcohols, phenols and amides useful as stabilizers for organic polymeric materials, and having the general formula:

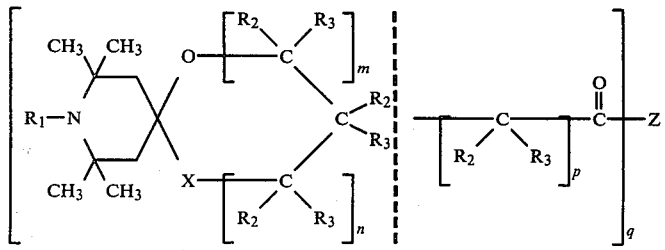

wherein:
$R_1$, $R_2$ and $R_3$ are selected from the group consisting of hydrogen and alkyl having from one to about eighteen carbon atoms;
X is oxygen or imino>NH;
m is zero, 1 or 2;
n is zero, 1 or 2;
m+n is 1 or 2;
p is zero or 1;
q is 1 to 6;

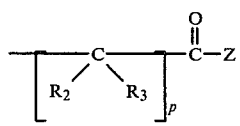

is linked to carbon in place of one $R_2$ or $R_3$ group.

The known piperidine compounds are also unsatisfactory in their stabilizing effectiveness, are volatile and lost from the polymer at high temperatures and are extracted by water.

In accordance with the present invention, polyethers containing 2,2,6,6-tetramethyl piperidinyl carboxylic

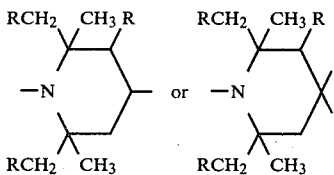

acid ester or ether groups are provided, comprising polymeric units having the structure

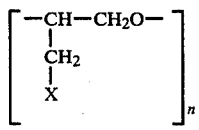

wherein
X is selected from the group consisting of:

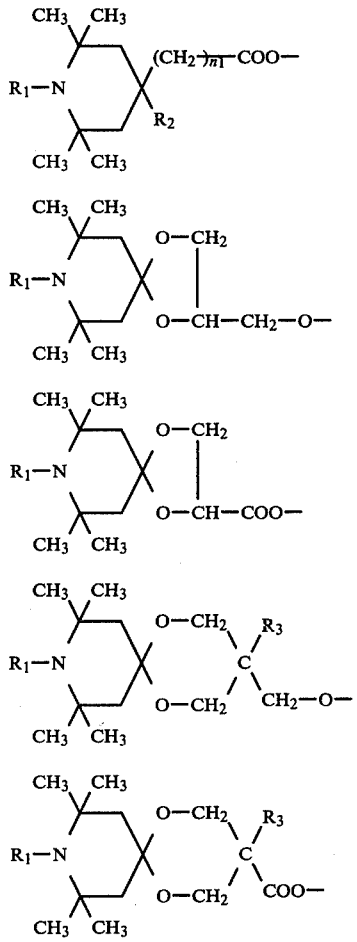

$R_1$ is selected from the group consisting of hydrogen, —O; alkyl, hydroxy alkyl and epoxyalkyl having from one to about eighteen carbon atoms, acyl having from one to about eighteen carbon atoms, cycloalkyl having from three to about eighteen carbon atoms; phenyl; phenalkyl and alkylphenyl having from seven to about twenty-four carbon atoms;

$R_2$ is hydrogen or hydroxy;

$n_1$ is 0 or 1;

$R_3$ is lower alkyl having from one to about six carbon atoms; and n is the average number of such units in the polymer; as well as stabilized synthetic resin compositions comprising such polyethers.

Exemplary $R_1$ alkyl are methyl, ethyl, propyl, isopropyl, butyl, isobutyl, tert-butyl, sec-butyl, amyl, isoamyl, tert amyl, hexyl, heptyl, octyl, isooctyl, 2-ethylhexyl, nonyl, isononyl, decyl, undecyl, dodecyl, palmityl, myristyl, stearyl, cyclopropyl, cyclobutyl, cyclopentyl, cyclohexyl, cycloheptyl, cyclooctyl, benzyl, phenethyl, phenbutyl, phenhexyl, tolyl, xylyl, mesityl, butylphenyl, octylphenyl, nonylphenyl, dodecylphenyl, 2-hydroxyethyl, 2-hydroxypropyl, 2-hydroxybutyl, 2,3-epoxypropyl, 2,3-epoxybutyl, 1,2-epoxy butyl, 1,2-epoxyamyl.

Exemplary $R_1$ acyl are acetyl, propionyl, butyroyl, octanoyl, lauroyl, stearoyl, palmitoyl and myristoyl.

Exemplary $R_3$ lower alkyl are methyl, ethyl, propyl, isopropyl, butyl, isobutyl, tert-butyl, isoamyl, amyl, hexyl and isohexyl.

The polyethers of this invention having the repeating unit represented by the Formula I can be easily prepared by chain-opening polymerization of glycidyl ethers and glycidyl esters containing a 2,2,6,6-tetramethylpiperidyl carboxy ester group, and having the formula

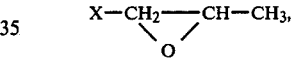

wherein X is as defined in Formula I to form polyethers having a polymerization degree of from 2 to 50, preferably from 3 to 20 (n=2 to 50, preferably 3 to 20).

Exemplary glycidyl ethers and glycidyl esters that can be used as raw material to prepare the polyethers of this invention include the glycidyl ethers of the alcohols disclosed in K. Murayama et al U.S. Pat. No. 4,212,974 and the glycidyl esters of the carboxylic acids disclosed in R. L. Hillard et al U.S. Pat. No. 4,064,102, Japan Kokai 74-58085 and M. Minagawa et al U.S. Pat. No. 4,336,183. They also can be easily prepared by the reaction of the alcohol or the carboxylic acid with the corresponding epihalohydrin or glycidol. Typical examples of starting glycidyl ethers and glycidyl esters and the polyethers resulting from polymerization thereof are shown below.

| Glycidyl Ether or Ester | Polyether |
|---|---|
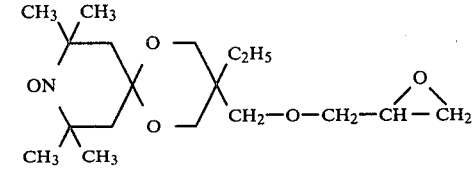

-continued

| | Glycidyl Ether or Ester | Polyether |
|---|---|---|
| 9. | (2,2,6,6-tetramethylpiperidin-4-yl with HN)—CH₂COO—CH₂—CH(—O—)CH₂ | [(2,2,6,6-tetramethylpiperidin-4-yl with HN)—CH₂CO—O—CH(CH₂O—)—CH₂—]ₙ |
| 10. | (2,2,6,6-tetramethyl-N-C₈H₁₇-piperidin-4-yl)—CH₂COO—CH₂—CH(—O—)CH₂ | [(2,2,6,6-tetramethyl-N-C₈H₁₇-piperidin-4-yl)—CH₂CO—O—CH(CH₂O—)—CH₂—]ₙ |
| 11. | (2,2,6,6-tetramethylpiperidin-4-yl with HN, spiro-dioxolane)—C(CH₃)—COO—CH₂—CH(—O—)CH₂ | [(2,2,6,6-tetramethylpiperidin-4-yl with HN, spiro-dioxolane)—C(CH₃)—CO—O—CH(CH₂O—)—CH₂—]ₙ |
| 12. | (2,2,6,6-tetramethyl-N-CH₃-piperidin-4-yl, spiro-dioxolane)—C(CH₃)—COO—CH₂—CH(—O—)CH₂ | [(2,2,6,6-tetramethyl-N-CH₃-piperidin-4-yl, spiro-dioxolane)—C(CH₃)—CO—O—CH(CH₂O—)—CH₂—]ₙ |
| 13. | (2,2,6,6-tetramethyl-N-O-piperidin-4-yl, spiro-dioxolane)—C(CH₃)—COO—CH₂—CH(—O—)CH₂ | [(2,2,6,6-tetramethyl-N-O-piperidin-4-yl, spiro-dioxolane)—C(CH₃)—CO—O—CH(CH₂O—)—CH₂—]ₙ |
| 14. | (2,2,6,6-tetramethylpiperidin-4-yl with HN, spiro-dioxolane)—COO—CH₂—CH(—O—)CH₂ | [(2,2,6,6-tetramethylpiperidin-4-yl with HN, spiro-dioxolane)—CO—O—CH(CH₂O—)—CH₂—]ₙ |
| 15. | (2,2,6,6-tetramethyl-N-CH₃-piperidin-4-yl, spiro-dioxolane)—COO—CH₂—CH(—O—)CH₂ | [(2,2,6,6-tetramethyl-N-CH₃-piperidin-4-yl, spiro-dioxolane)—CO—O—CH(CH₂O—)—CH₂—]ₙ |

| Glycidyl Ether or Ester | Polyether |
|---|---|
| 16. [structure: 2,2,6,6-tetramethyl-N-acetyl-4-piperidinyl spiro dioxane with -COO-CH₂-CH(-O-)CH₂ glycidyl ester] | [structure: corresponding polyether repeat unit with -CH-CH₂O- and -CO-O-, subscript n] |

The starting glycidyl ethers and esters can easily be polymerized by conventional methods of which the following illustrate preferred embodiments.

EXAMPLE I

Synthesis of polymer of 9-aza-3-ethyl-8,8,9,10,10-pentamethyl-1,5-dioxaspiro[5,5]-3-undecylmethyl glycidyl ether (No. 1 above).

9-Aza-3-ethyl-8,8,9,10,10-pentamethyl-1,5-dioxaspiro[5,5]-3-undecylmethyl glycidyl ether, 1.7 g, potassium-t-butoxide 0.04 g and dioxane 2 ml were heated and stirred at 150° C. for 3 hours under a stream of nitrogen. Chloroform was added, and the solution filtered through a layer of Kyowaad 700 (Kyowa Chemical Co.; synthetic absorbent).

The solvent was evaporated, and 1.7 g of pale yellow semisolid (Stabilizer No. 1) was obtained. Molecular weight=1700. (polymerization degree n=5)

The following polymers were prepared by the same procedure as in Example I:

| Glycidyl Ether or Ester | Polyether | Molecular Weight | Polymerization Degree |
|---|---|---|---|
| [structure with N-O, C₂H₅, CH₂-O-CH₂-CH(-O-)CH₂] | [corresponding polyether]ₙ | 1500 | 4 |
| [structure with CH₃C(=O)N, C₂H₅, CH₂-O-CH₂-CH(-O-)CH₂] | [corresponding polyether]ₙ | 3000 | 8 |
| [structure with CH₃N, CH₃, CH₂-O-CH₂-CH(-O-)CH₂] | [corresponding polyether]ₙ | 2500 | 8 |
| [structure with CH₃N, CH₂-O-CH₂-CH(-O-)CH₂] | [corresponding polyether]ₙ | 2300 | 8 |
| [structure with HN, OH, COO-CH₂-CH(-O-)CH₂] | [corresponding polyether]ₙ | 2000 | 8 |

-continued

| Glycidyl Ether or Ester | Polyether | Molecular Weight | Polymerization Degree |
|---|---|---|---|
| [piperidine with 2,2,6,6-tetramethyl, NH, 4-COO-CH₂-CH(O)-CH₂ (glycidyl ester)] | [−(CH−CH₂O)−]ₙ with CH₂ bridging to CO−O, piperidine 2,2,6,6-tetramethyl, HN | 2000 | 8 |
| [piperidine 2,2,6,6-tetramethyl, N-CH₃, 4-COO-CH₂-CH(O)-CH₂] | [−(CH−CH₂O)−]ₙ, CH₂, CO−O, piperidine 2,2,6,6-tetramethyl, CH₃N | 2800 | 11 |
| [piperidine 2,2,6,6-tetramethyl, HN, 4-CH₂COO-CH₂-CH(O)-CH₂] | [−(CH−CH₂O)−]ₙ, CH₂, CH₂CO−O, piperidine 2,2,6,6-tetramethyl, HN | 1800 | 7 |
| [piperidine 2,2,6,6-tetramethyl, C₈H₁₇N, 4-CH₂COO-CH₂-CH(O)-CH₂] | [−(CH−CH₂O)−]ₙ, CH₂, CH₂CO−O, piperidine 2,2,6,6-tetramethyl, C₈H₁₇N | 3400 | 9 |
| [piperidine 2,2,6,6-tetramethyl, HN, 4-spiro dioxane with CH₃, COO-CH₂-CH(O)-CH₂] | [−(CH−CH₂O)−]ₙ with CH₃, CH₂, CO−O, spiro dioxane, piperidine 2,2,6,6-tetramethyl, HN | 1700 | 5 |
| [piperidine 2,2,6,6-tetramethyl, CH₃N, 4-spiro dioxane CH₃, COO-CH₂-CH(O)-CH₂] | [−(CH−CH₂O)−]ₙ, CH₃, CH₂, CO−O, spiro dioxane, piperidine 2,2,6,6-tetramethyl, CH₃N | 2600 | 7 |
| [piperidine 2,2,6,6-tetramethyl, N-O, 4-spiro dioxane CH₃, COO-CH₂-CH(O)-CH₂] | [−(CH−CH₂O)−]ₙ, CH₃, CH₂, CO−O, spiro dioxane, piperidine 2,2,6,6-tetramethyl, ON | 2000 | 6 |

| Glycidyl Ether or Ester | Polyether | Molecular Weight | Polymerization Degree |
|---|---|---|---|
| [structure: HN-piperidyl-COO-CH2-CH-CH2 epoxide with CH3 groups] | [structure: HN-piperidyl polyether -CO-O-CH2-CH(CH2)-CH2O-]n | 1500 | 5 |
| [structure: CH3N-piperidyl-COO-CH2-CH-CH2 epoxide] | [structure: CH3N-piperidyl polyether] | 3000 | 9 |
| [structure: CH3CN(=O)-piperidyl-COO-CH2-CH-CH2 epoxide] | [structure: CH3CN(=O)-piperidyl polyether] | 4500 | 13 |

Small amounts of the polyether piperidyl esters and ethers of this invention when combined with synthetic resin improve the light stability of the resin. The amount of the polyether piperidyl ether or ester is generally within the range from about 0.001 to about 5 parts by weight, preferably from about 0.01 to about 3 parts by weight, per 100 parts by weight of resin.

Synthetic resins that can have their resistance to deterioration enhanced with polyether piperidyl esters and ethers according to this invention include α-olefin polymers such as polyethylene, polypropylene, polybutene, poly-3-methylbutene, or mixtures thereof, and copolymers with other monomers such as ethylene-vinyl acetate copolymer; ethylene-propylene copolymer; polystyrene; polyvinyl acetate; polyacrylic esters; copolymers from styrene and another monomer (for example, maleic anhydride, butadiene, and acrylonitrile); acrylonitrile-butadiene-styrene copolymer, acrylic acid ester-butadiene-styrene copolymer, methacrylic acid ester-butadiene-styrene copolymer, polymethacrylate esters such as polymethacrylate; polyvinyl alcohol; polyvinyl formal; polyvinyl butyral; linear polyesters, polyamides; polycarbonates; polyacetals; polyurethanes; cellulosic resins; phenol-formaldehyde resins; urea-formaldehyde resins; melamine-formaldehyde resins; epoxy resins; unsaturated polyester resins; silicone resins; halogen-containing resins such as polyvinyl chloride, polyvinylidene chloride, polyvinylidene fluoride, and copolymers thereof, and rubbers such as isoprene rubber, butadiene rubber, epichlorohydrin rubber, chloroprene rubber, and blends of any of the above.

The polyether piperidyl esters and ethers of the invention can be combined with conventional heat stabilizers such as phenolic antioxidants, polyvalent metal salts of organic acids, organic phosphites, thioethers, and other known heat stabilizers, thereby constituting light and heat stabilizer compositions of the invention.

The phenolic antioxidant contains one or more phenolic hydroxyl groups, and one or more phenolic nuclei, and can contain from about eight to about three hundred carbon atoms. In addition, the phenolic nucleus can contain an oxy or thio ether group.

The alkyl-substituted phenols and polynuclear phenols, because of their molecular weight, have a higher boiling point, and therefore are preferred because of their lower volatility. There can be one or a plurality of alkyl groups of one or more carbon atoms. The alkyl group or groups including any alkylene groups between phenol nuclei preferably aggregate at least four carbon atoms. The longer the alkyl or alkylene chain, the better the compatibility with polypropylene, inasmuch as the phenolic compound then acquires more of an aliphatic hydrocarbon character, and therefore there is no upper limit on the number of alkyl carbon atoms. Usually, from the standpoint of availability, the compound will not have more than about eighteen carbon atoms in an alkyl, alicyclidene and alkylene group, and a total of not over about fifty carbon atoms. The compounds may have from one to four alkyl radicals per phenol nucleus.

The phenol contains at least one and preferably at least two phenolic hydroxyls, the two or more hydroxyls being in the same ring, if there is only one. In the case of bicyclic phenols, the rings can be linked by thio or oxyether groups, or by alkylene, alicyclidene or arylidene groups.

The monocyclic phenols which can be employed have the structure:

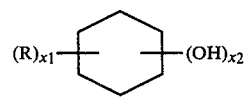

R is selected from the group consisting of hydrogen; halogen; and organic radicals containing from one to about thirty carbon atoms, such as alkyl, aryl, alkenyl, alkaryl, aralkyl, cycloalkenyl, cycloalkyl, alkoxy, and acyl $$(R'C-)_7$$
$$\phantom{(R'C}\|\phantom{-)_7}$$
$$\phantom{(R'C}O\phantom{-)_7}$$

where R' is aryl, alkyl or cycloalkyl.

$x_1$ and $x_2$ are integers from one to four, and the sum of $x_1$ and $x_2$ does not exceed six.

The polycyclic phenol phenol is one having at least two aromatic nuclei linked by a polyvalent linking radical, as defined by the formula:

$$(Ar)_{n1}-Y-(Ar)_{n2}$$
$$\phantom{(}|\phantom{_{n1}-Y-}|$$
$$(OH)_{m1}\phantom{-Y-}(OH)_{m2}$$

wherein

Y is a polyvalent linking group selected from the group consisting of oxygen; carbonyl; sulfur; sulfinyl; aromatic, aliphatic and cycloaliphatic hydrocarbon groups; and oxyhydrocarbon, thiohydrocarbon and heterocyclic groups. The linking group can have from one up to twenty carbon atoms.

Ar is a phenolic nucleus which can be a phenyl or a polycarbocyclic group having condensed or separate phenyl rings; each Ar group contains at least one free phenolic hydroxyl group up to a total of five. The Ar rings can also include additional rings connected by additional linking nuclei of the type Y, for example, Ar—Y—Ar—Y—Ar.

$m_1$ and $m_2$ are numbers from one to five, and $n_1$ and $n_2$ are numbers of one or greater, and preferably from one to four.

The aromatic nucleus Ar can, in addition to phenolic hydroxyl groups, include one or more inert substituents. Examples of such inert substituents include hydrogen; halogen atoms, e.g., chlorine, bromine and fluorine; organic radicals containing from one to about thirty carbon atoms, such as alkyl, aryl, alkaryl, aralkyl, cycloalkenyl, cycloalkyl, alkoxy, aryloxy and acyloxy $$(R'C-O)$$
$$\phantom{(R'}\|\phantom{-O)}$$
$$\phantom{(R'}O\phantom{-O)}$$

where R' is aryl, alkyl or cycloalkyl, or thiohydrocarbon groups having from one to about thirty carbon atoms, and carboxyl $$(-C-O-)$$
$$\phantom{(-}\|\phantom{-O-)}$$
$$\phantom{(-}O\phantom{-O-)}$$

groups. Usually, however, each aromatic nucleus will not have more than about eighteen carbon atoms in any hydrocarbon substituent group. The Ar group can have from one to four substituent groups per nucleus.

Typical aromatic nuclei include phenyl, naphthyl, phenanthryl, triphenylenyl, anthracenyl, pyrenyl, chrysenyl, and fluoroenyl groups.

When Ar is a benzene nucleus, the polyhydric polycyclic phenol has the structure:

$$\left[\underset{(R_1)_{x1}}{\underset{|}{\bigcirc}}\overset{(OH)_{m1}}{\phantom{\bigcirc}}-Y-\left[\underset{(R_2)_{x2}}{\underset{|}{\bigcirc}}\overset{(OH)_{m2}}{\phantom{\bigcirc}}-Y-\right]_{y1}\underset{(R_3)_{x3}}{\underset{|}{\bigcirc}}\overset{(OH)_{m3}}{\phantom{\bigcirc}}\right]_{y2}$$

wherein $R_1$, $R_2$ and $R_3$ are inert substituent groups as described in the previous paragraph;

$m_1$ and $m_3$ are integers from one to a maximum of five;

$m_2$ is an integer from one to a maximum of four;

$x_1$ and $x_3$ are integers from zero to four, and $x_2$ is an integer from zero to three;

$y_1$ is an integer from zero to about six and $y_2$ is an integer from one to five, preferably one or two.

Preferably, the hydroxyl groups are located ortho and/or para to Y.

Exemplary Y groups are alkylene, alkylidene, and alkenylene; arylene, alkyl arylene, arylalkylene; cycloalkylene, cycloalkylidene; and oxa- and thia-substituted such groups; tetrahydrofuranes, esters and triazino groups. The Y groups are usually bi, tri, or tetravalent, connecting two, three or four Ar groups. However, higher valency Y groups connecting more than four Ar groups, can also be used. According to their constitution, the Y groups can be assigned to subgenera as follows:

(1) Y groups where at least one carbon in a chain or cyclic arrangement connect the aromatic groups, such as: —CH₂—CH₂—; —(CH₂)₅—; —CH₂—;

-continued

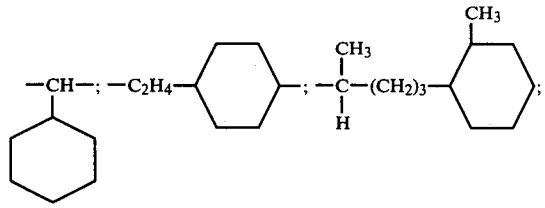

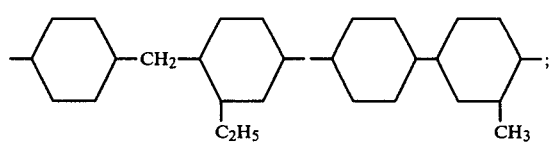

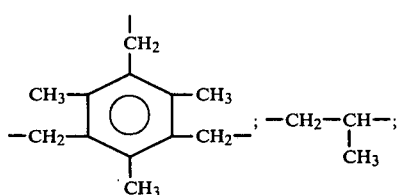

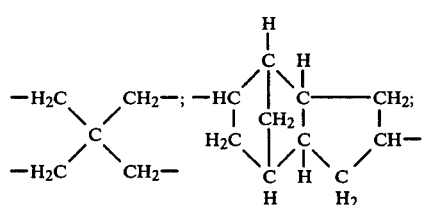

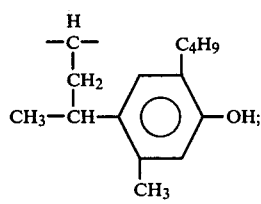

(2) Y groups where only atoms other than carbon link the aromatic rings, such as —O—, —S—,

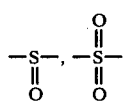

and —(S)$_x$— where x is a number from one to ten;

(3) Y groups made up of more than a single atom including both carbon and other atoms linking the aromatic nuclei, such as:

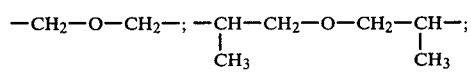

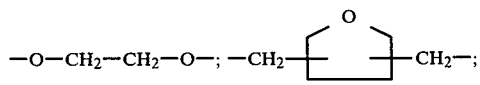

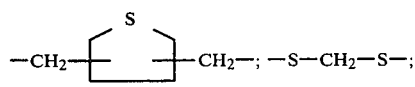

-continued

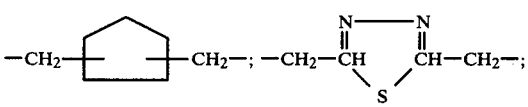

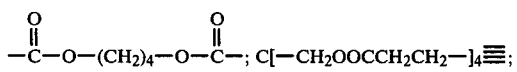

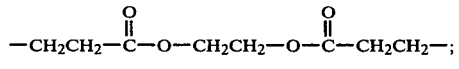

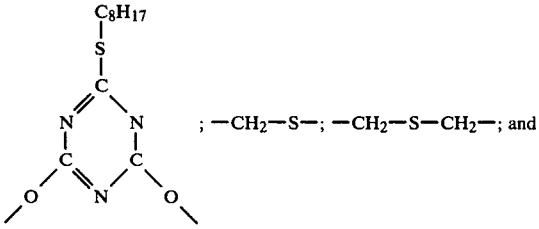

Although the relation of effectiveness to chemical structure is insufficiently understood, many of the most effective phenols have Y groups of subgenus 1), and accordingly this is preferred. Some of these phenols can be prepared by the alkylation of phenols or alkyl phenols with polyunsaturated hydrocarbons such as dicyclopentadiene or butadiene.

Representative phenols include guaiacol, resorcinol monoacetate, vanillin, butyl salicylate, 2,6-di-tert-butyl-4-methyl phenol, 2-tert-butyl-4-methoxy phenol, 2,4-dinonyl phenol, 2,3,4,5-tetradecyl phenol, tetrahydro-α-naphthol, o-, m- and p-cresol, o-, m- and p-phenylphenol, o-, m- and p-xylenols, the carvenols, symmetrical xylenol, thymol, o-, m- and p-nonylphenol, o-, m- and p-dodecyl-phenol, and o-, m- and p-octyl-phenol, o-, and m-tert-butyl-p-hydroxy-anisole, p-n-decyloxyphenol, p-n-decyloxy-cresol, nonyl-n-decyloxycresol, eugenol, isoeugenol, glyceryl monosalicylate, methyl-p-hydroxy-cinnamate, 4-benzyloxy-phenol, p-acetylaminophenol, p-stearyl-aminophenol, methyl-p-hydroxybenzoate, p-dichlorobenzoyl-aminophenol, p-hydroxysalicyl anilide, -stearyl-(3,5-di-methyl-4-hydroxy-benzyl)thioglycolate, stearyl-β-(4-hydroxy-3,5-di-t-butylphenyl)propionate, distearyl-3,5-di-t-butyl-4-hydroxybenzylphosphonate, and distearyl (4-hydroxy-3-methyl-5-t-butyl)benzylmalonate.

Exemplary polyhydric phenols are orcinol, propyl gallate, catechol, resorcinol, 4-octyl-resorcinol, 4-dodecylresorcinol, 4-octadecyl-catechol, 4-isooctyl-phloroglucinol, pyrogallol, hexahydroxybenzene, 4-isohexylcatechol, 2,6-ditertiary-butyl-resorcinol, 2,6-diisopropyl-phloroglucinol.

Exemplary polyhydric polycyclic phenols are methylene bis-(2,6-di-tertiary-butyl-phenol), 2,2-bis-(4-hydroxy phenyl)propane, methylene-bis-(p-cresol), 4,4'-benzylidene bis (2-tertiary-butyl-5-methyl-phenol), 4,4'-cyclo-hexylidene bis-(2-tertiary-butylphenol), 2,2'-methylene-bis-(4-methyl-6-(1'-methyl-cyclohexyl)- phenol), 2,6-bis-(2'-hydroxy-3'-tertiarybutyl-5'-methylbenzyl)-4-methylphenol, 4,4'-bis-(2-tertiarybutyl-5-methyl-phenol), 2,2'-bis-(4-hydroxy-phenyl)butane, ethylene bis-(p-cresol), 4,4'-oxobis-phenol, 4,4'-oxobis(3-methyl-5-isopropyl-phenol), 4,4'-oxobis-(3-methyl-phenol), 2,2'-oxobis-(4-dodecyl-phenol), 2,2'-oxobis-(4-methyl-5-tertiary-butyl-phenol), 4,4'-thio-bis-phenol; 4,4'-thio-bis(3-methyl-6-tertiary-butyl-phenol), 2,2'-thio-bis-(4-methyl-6-tertiary-butyl-phenol), 4,4'-n-butylidene-(2-t-butyl-5-methylphenol), 2,2'-methylene-bis-(4-methyl-6-(1'-methyl-cyclohexyl)phenol), 4,4'-cyclohexylene bis-(2-tertiary-butyl-phenol), 2,6-bis-(2'-hydroxy-3'-t-butyl-5'-methyl-benzyl)-4-methyl-phenol, 4,4'-oxobis(naphthalene-1,5-diol), 1,3'-bis-(naphthalene-2,5-diol)propane, and 2,2'-butylene bis-(naphthalene-2,7-diol), (3-methyl-5-tert-butyl-4-hydroxyphenyl)-4'-hydroxy-phenyl)propane, 2,2'-methylene-bis-(4-methyl-5-isopropylphenol), 2,2'-methylene-bis-(4-methyl-5-isopropylphenol), 2,2'-methylene-bis-(5-tert-butyl-4-chlorophenol), (3,5-di-tert-butyl-4-hydroxyphenyl)-(4'-hydroxyphenyl)ethane, (2-hydroxy-phenyl)(3',5'-di-tert-butyl-4',4-hydroxyphenyl)ethane, 2,2'-methylene-bis-(4-octylphenol), 4,4'-propylene-bis-(2-tert-butylphenol), 2,2'-isobutylene-bis-(4-nonylphenol), 2,4-bis-(4-hydroxy-3-t-butyl-phenoxy)-6-(n-octylthio)-1,3,5-triazine, 2,4,6-tris-(4-hydroxy-3-t-butyl-phenoxy)-1,3,5-triazine, 2,2'-bis-(3-t-butyl-4-hydroxyphenyl)thiazolo-(5,4-d)thiazole, 2,2'-bis-(3-methyl-5-t-butyl-4-hydroxyphenyl)thiazolo-(5,4-d)-thiazole, 4,4'-bis-(4-hydroxyphenyl)pentanoic acid octadecyl ester, cyclopentylene-4,4'-bis-phenol, 2-ethylbutylene-4,4'-bisphenol, 4,4'-cyclooctylene-bis-(2-cyclohexylphenol), β,β-thiodiethanolbis-(3-tert-butyl-4-hydroxyphenoxy acetate), 1,4-butanediobis-(3-tert-butyl-4-hydroxyphenoxy acetate), pentaerythritol tetra-(4-hydroxyphenol propionate), 2,4,4'-tri-hydroxy benzophenone, bis-(2-tert-butyl-3-hydroxy-5-methylphenyl)sulfide, bis-(2-tert-butyl-4-hydroxy-5-methylphenyl)sulfide, bis-(2-tert-butyl-4-hydroxy-5-methylphenyl)sulfoxide, bis-(3-ethyl-5-tert-butyl-4-hydroxybenzyl)sulfide, bis-(2-hydroxy-4-methyl-6-tert-butyl-phenyl)sulfide, 4,4'-bis-(4-hydroxyphenol)pentanoic acid octadecyl thiopropionate ester, 1,1,3-tris-(2'-methyl-4-hydroxy-5'-tert-butylphenyl)butane, 1,1,3-tris-(1-methyl-3-hydroxy-4-tert-butylphenyl)butane, 1,8-bis-(2-hydroxy-5-methylbenzoyl-n-octane, 2,2'-ethylenebis-[4'-(3-tert-butyl-4-hydroxyphenyl)-thiazol], 1-methyl-3-(3-methyl-5-tert-butyl-4-hydroxybenzyl)-naphthalene, 2,2'-(2-butene)-bis-(4-methoxy-6-tert-butylphenol)-bis-[3,3-bis-(4-hydroxy-3-t-butylphenyl)butyric acid] glycol ester, 4,4'-butylidene-bis-(6-t-butyl-m-cresol), 1,1,3-tris-(2-methyl-4-hydroxy-5-t-butylphenyl)butane, 1,3,5-tris-(3,5-di-t-butyl-4-hydroxybenzyl)-2,4,6-trimethylbenzene, tetrakis[methylene-3(3,5-di-t-butyl-4-hydroxyphenyl)propionate]methane, 1,3,5-tris-(3,5-di-t-butyl-4-hydroxybenzyl)isocyanurate, 1,3,5-tris(3,5-di-t-butyl-4-hydroxyphenyl)propionyl-oxyethyl isocyanurate, 2-octylthio-4,6-di-(4-hydroxy-3,5-di-t-butyl)phenoxy-1,3,5-triazine, 4,4'-thiobis-(6-t-butyl-m-cresol) and pentaerythritol hydroxyphenyl propionate.

A particularly desirable class of polyhydric polycyclic phenols are the dicyclopentadiene polyphenols, which are of the type:

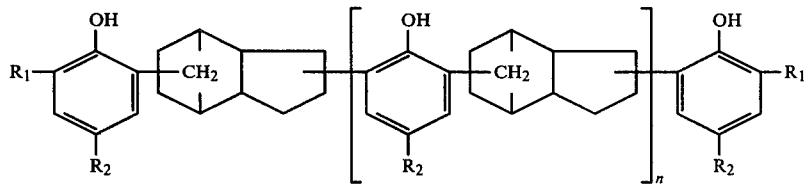

in which

R₁ and R₂ are lower alkyl, and can be the same or different, and n is the number of the groups enclosed by the brackets, and is usually from 1 to about 5. These are described in U.S. Pat. No. 3,567,683, dated Mar. 2, 1971 to Spacht. A commercially available member of this class is Wingstay L, exemplified by dicyclopentadiene tri-(2-tert-butyl-4-methyl-phenol) of the formula:

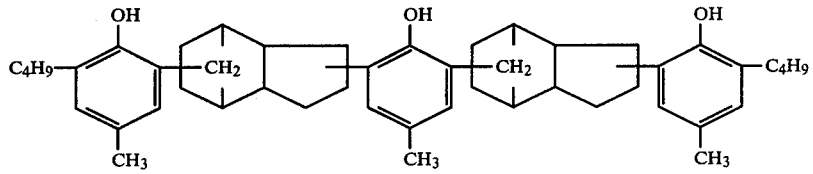

The polyhydric polycyclic phenols used in the invention can also be condensation products of phenols or alkylphenols with hydrocarbons having a bicyclic ring structure and a double bond or two or more double bonds, such as α-pinene, β-pinene, dipentene, limonene, vinylcyclohexene, dicyclopentadiene, allo-ocimene, isoprene and butadiene. These condensation products are usually obtained under acidic conditions in the form of more or less complex mixtures of monomeric and polymeric compounds. However, it is usually not necessary to isolate the individual constituents. The entire reaction product, merely freed from the acidic condensation catalyst and unchanged starting material, can be used with excellent results. While the exact structure of these phenolic condensation products is uncertain, the Y groups linking the phenolic nuclei all fall into the preferred subgenus 1. For method of preparation, see e.g., U.S. Pat. Nos. 3,124,555, 3,242,135, and British Pat. No. 961,504.

When the polyether piperidyl ester or ether is used with a polyvalent metal salt of an organic acid, the organic acid will ordinarily have from about six to about twenty-four carbon atoms. The polyvalent metal can be any metal of Group II of the Periodic Table, such as zinc, calcium, cadmium, barium, magnesium and strontium. The alkali metal salts and heavy metal salts such as lead salts are unsatisfactory. The acid can be any organic non-nitrogenous monocarboxylic acid having from six to twenty-four carbon atoms. The aliphatic, aromatic, alicyclic and oxygen-containing heterocyclic organic acids are operable as a class. By the term "aliphatic acid" is meant any open chain carboxylic acid, substituted, if desired, with nonreactive groups, such as halogen, sulfur and hydroxyl. By the term "alicyclic" it will be understood that there is intended any cyclic acid in which the ring is nonaromatic and composed solely of carbon atoms, and such acids may if desired have inert, nonreactive substituents such as halogen, hydroxyl, alkyl radicals, alkenyl radicals and other carbocyclic ring structures condensed therewith. The oxygen-containing heterocyclic compounds can be aromatic or nonaromatic and can include oxygen and carbon in the ring structure, such as alkyl-substituted furoic acid. The aromatic acids likewise can have nonreactive ring substituents such as halogen, alkyl and alkenyl groups, and other saturated or aromatic rings condensed therewith.

As exemplary of the acids which can be used in the form of their metal salts there can be mentioned the following: hexoic acid, 2-ethylhexoic acid, n-octoic acid, isooctoic acid, capric acid, undecylic acid, lauric acid, myristic acid, palmitic acid, margaric acid, stearic acid, oleic acid, ricinoleic acid, behenic acid, chlorocaproic acid, hydroxy capric acid, benzoic acid, phenylacetic acid, butyl benzoic acid, ethyl benzoic acid, propyl benzoic acid, hexyl benzoic acid, salicylic acid, naphthoic acid, 1-naphthalene acetic acid, orthobenzoyl benzoic acid, naphthenic acids derived from petroleum, abietic acid, dihydroabietic acid, hexahydrobenzoic acid, and methyl furoic acid.

The water-insoluble salts are preferred, because they are not leached out when the plastic is in contact with water. Where these salts are not known, they are made by the usual types of reactions, such as by mixing the acid, or anhydride with the corresponding oxide or hydroxide of the metal in a liquid solvent, and heating, if necessary, until salt formation is complete.

A variety of organic triphosphites and acid phosphites can be employed, of which the following are exemplary.

The organic triphosphite can be any organic phosphite having three or more organic radicals attached to phosphorus through oxygen. The acid phosphite can be any organic phosphite having one or two organic radicals attached to phosphorus through oxygen. These radicals can be monovalent radicals, in the case of the triphosphites, diphosphites and monophosphites.

The organic triphosphites in which the radicals are monovalent radicals can be defined by the formula:

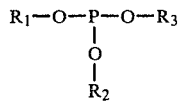

in which $R_1$, $R_2$ and $R_3$ are selected from the group consisting of alkyl, alkenyl, aryl, alkaryl, aralkyl, and cycloalkyl groups having from one to about thirty carbon atoms.

The acid phosphites are defined by the same formula, but one or two of $R_1$, $R_2$ and $R_3$ is hydrogen or a cation of a metal or ammonium.

Also included are the organic triphosphites having a bivalent organic radical forming a heterocyclic ring with the phosphorus of the type:

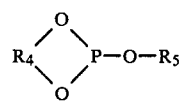

in which
$R_4$ is a bivalent organic radical selected from the group consisting of alkylene, arylene, aralkylene, alkarylene and cycloalkylene radicals having from two to about thirty carbon atoms, and $R_5$ is a monovalent organic radical as defined above in the case of $R_1$, $R_2$ and $R_3$;
$R_5$ is hydrogen or a cation, in the case of the acid phosphites.

Also useful organic triphosphites are mixed heterocyclic-open chain phosphites of the type:

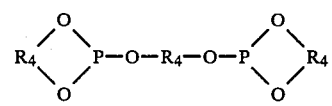

More complex triphosphites are formed from trivalent organic radicals, of the type:

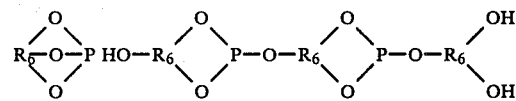

in which $R_6$ is a trivalent organic radical of any of the types of $R_1$ to $R_5$, inclusive, as defined above.

A particularly useful class of complex triphosphites are the tetraoxadiphosphaspiro undecanes of the formula:

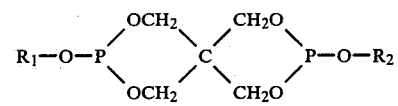

where $R_1$ and $R_2$ are selected from the group consisting of aryl, alkyl, aryloxyethyl, alkyloxyethyl, aryloxyethoxyethyl, alkyloxyethoxyethyl and alkyloxypolyethoxyethyl having from about 1 to about 30 carbon atoms.

In the case of the acid phosphites, one or both of $R_1$ and $R_2$ is also hydrogen or a cation.

An especially preferred class of organic triphosphites and acid phosphites have a bicyclic aromatic group attached to phosphorus through oxygen, with no or one or more phenolic hydroxyl groups on either or both of the aromatic rings. These phosphites are characterized by the formula:

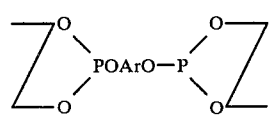

or

-continued

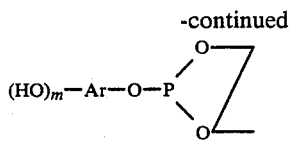

in which Ar is a mono or bicyclic aromatic nucleus and m is an integer of from 0 to about 5. Z is one or a plurality of organic radicals as defined above for $R_1$ to $R_6$, taken singly or together in sufficient number to satisfy the valences of the two phosphite oxygen atoms.

One or both Z radicals is also hydrogen, in the case of the acid phosphites, and can include additional bicyclic aromatic groups of the type $(HO)_m$-Ar.

The cation in the case of said phosphites can be a metal, such as an alkali metal, for instance, sodium, potassium or lithium; an alkaline earth metal, for instance, barium, calcium, or a nontoxic polyvalent metal, such as magnesium, tin and zinc.

Usually, the triphosphites and acid phosphites will not have more than about sixty carbon atoms.

Exemplary triphosphites are monophenyl di-2-ethylhexyl phosphite, diphenyl mono-2-ethylhexyl phosphite, di-isooctyl monotolyl phosphite, tri-2-ethylhexyl phosphite, phenyl dicyclohexyl phosphite, phenyl diethyl phosphite, triphenyl phosphite, tricresyl phosphite, tri(dimethylphenyl)phosphite, trioctadecyl phosphite, triisooctyl phosphite, tridodecyl phosphite, isooctyl diphenyl phosphite, diisooctyl phenyl phosphite, tri(t-octylphenyl)phosphite, tri-(t-nonylphenyl)phosphite, benzyl methyl isopropyl phosphite, butyl dicresyl phosphite, isooctyl di(octylphenyl)phosphite, di(2-ethylhexyl)(isooctylphenyl)phosphite, tri(2-cyclohexylphenyl)phosphite), tri-α-naphthyl phosphite, tri(-phenylphenyl)phosphite, tri(2-phenylethyl)phosphite, ethylene phenyl phosphite, ethylene t-butyl phosphite, ethylene isohexyl phosphite, ethylene isooctyl phosphite, ethylene cyclohexyl phosphite, 2-phenoxy-1,3,2-dioxaphosphorinane, 2-butoxy-1,3,2-dioxyphosphorinane, 2-octoxy-5,5-dimethyl-dioxaphosphorinane, and 2-cyclohexyloxy-5,5-diethyl dioxaphosphorinane.

Exemplary pentaerythritol triphosphites are 3,9-diphenoxy-2,4,8,10-tetraoxa-3,9-diphosphaspiro-(5,5)-undecane (diphenyl-pentaerythritol diphosphite), 3,9-di(decyloxy)-2,4,8,10-tetraoxa-3,9-diphosphaspiro(5,5)-undecane, 3,9-di(isodecyloxy)-2,4,8,10-tetraoxa-3,9-diphosphaspiro-(5,5)-undecane, 3,9-di(octadecyloxy)-2,4,8,10-tetraoxa-3,9-diphosphaspiro-(5,5)-undecane, 3-phenoxy-9-isodecyloxy-2,4,8,10-tetraoxa-3,9-diphosphaspiro-(5,5)-undecane, 3,9-di(methoxy)-2,4,8,10-tetraoxa-3,9-diphosphaspiro-(5,5)-undecane, 3,9-di(-lauryloxy)-2,4,8,10-tetraoxa-3,9-diphosphaspiro-(5,5)-undecane, 3,9-di-p-tolyloxy-2,4,8,10-tetraoxa-3,9-diphosphaspiro-(5,5)-undecane, 3,9-di(methoxyethyloxy)-2,4,8,10-tetraoxa-3,9-diphosphaspiro-(5,5)-undecane, 3-methoxyethyloxy-9-isodecyloxy-2,4,8,10-tetraoxa-3,9-diphosphaspiro-(5,5)-undecane, 3,9-di(ethoxyethyloxy)-2,4,8,10-tetraoxa-3,9-diphosphaspiro-(5,5)-undecane, 3,9-di(butoxyethyloxy)-2,4,8,10-tetraoxa-3,9-diphosphaspiro-(5,5)-undecane, 3-methoxyethyloxy-9-butoxy-ethyloxy-2,4,8,10-tetraoxa-3,9-diphosphaspiro-(5,5)-undecane, 3,9-di(methoxyethoxyethyloxy)-2,4,8,10-tetraoxa-3,9-diphosphaspiro-(5,5)-undecane, 3,9-di(butoxyethoxyethyloxy)-2,4,8,10-tetraoxa-3,9-diphosphaspiro-(5,5)-undecane, 3,9-di(methoxyethoxyethoxyethyloxy)-2,4,8,10-tetraoxa-3,9-diphosphaspiro-(5,5)-undecane, 3,9-di(methoxy(polyethoxy)ethyloxy)-2,4,8,10-tetraoxa-3,9-diphosphaspiro-(5,5)-undecane where the (polyethoxy) ethyloxy group has an average molecular weight of 350),3,9-di(methoxy(polyethoxy)ethyloxy)-2,4,8,10-tetraoxa-3,9-diphosphaspiro-(5,5)-undecane (where the (polyethoxy) ethyloxy group has an average molecular weight of 550).

Exemplary of the bis aryl triphosphites are: bis(4,4'-thio-bis(2-tertiary-butyl-5-methyl-phenol)) isooctyl phosphite, mono(4,4'-thio-bis(2-tertiary-butyl-5-methyl-phenol)) di-phenyl phosphite, tri-(4,4'-n-butylidene-bis(2-tertiary-butyl-5-methyl-phenol)) phosphite, (4,4'-benzylidene-bis(2-tertiary-butyl-5-methyl-phenol)) di-phenyl phosphite, isooctyl 2,2'-bis(-para-hydroxyphenyl)propane phosphite, decyl 4,4'-n-butylidene-bis(2-tertiary-butyl-5-methylphenol)phosphite, tri-4,4'-thio-bis(2-tertiary-butyl-5-methylphenol)phosphite, 2-ethylhexyl-2,2'-methylene-bis(4-methyl-6,1'-methylcyclohexyl)phenol phosphite, tri(2,2'-bis-(para-hydroxyphenyl)propane)phosphite, tri(4,4'-thio-bis(2-tertiary-butyl-5-methyl-phenol)phosphite, isooctyl(2,6-bis(2'-hydroxy-3,5-dinonylbenzyl)-4-nonyl phenyl)) phosphite, tetra-tridecyl-4,4'-n-butylidene-bis(2-tertiary-butyl-5-methylphenyl)diphosphite, tetra-isooctyl-4,4'-thio-bis(2-tertiary-butyl-5-methylphenyl)diphosphite, 2,2'-methylene-bis(4-methyl-6,1'-methyl cyclohexyl phenyl)polyphosphite, isooctyl-4,4'-isopropylidene-bisphenyl polyphosphite, 2-ethylhexyl-2,2'-methylene-bis(4-methyl-6,1'-methyl-cyclohexyl)phenyl triphosphite, tetra-tridecyl-4,4'-oxydiphenyl diphosphite, tetra-n-dodecyl-4,4'-n-butylidene bis(2-tertiarybutyl-5-methylphenyl)diphosphite, tetra-tridecyl-4,4'-isopropylidene bisphenyl diphosphite, hexa-tridecyl butane-1,1,3-tris(2'-methyl-5'-tertiary-butylphenyl-4')triphosphite.

Exemplary acid phosphites are di(phenyl)phosphite, monophenyl phosphite, mono(diphenyl)phosphite, dicresyl phosphite, di-(o-isooctylphenyl)phosphite, di(p-ethylhexylphenyl)phosphite, di(p-t-octylphenyl)phosphite, di(dimethylphenyl)phosphite, di-n-butyl phosphite, di-2-ethylhexyl phosphite, mono-2-ethylhexylphosphite, diisooctyl phosphite, monoisooctyl phosphite, monododecyl phosphite, 2-ethylhexyl phenyl phosphite, 2-ethylhexyl-(n-octylphenyl)phosphite, monocyclohexyl phosphite, dicyclohexyl phosphite, di(2-cyclohexyl phenyl)phosphite, di-α-naphthyl phosphite, diphenyl phenyl phosphite, di(diphenyl)phosphite, di-(2-phenyl ethyl)phosphite, dibenzyl phosphite, monobenzyl phosphite, n-butyl cresyl phosphite and didodecyl phosphite, cresyl phosphite, t-octylphenyl phosphite, ethylene phosphite, butyl cresyl phosphite, isooctyl monotolyl phosphite and phenyl cyclohexyl phosphite.

Exemplary of the bis aryl acid phosphites are: bis(4,4'-thio-bis(2-tertiary-butyl-5-methylphenol)) phosphite, (4,4'-thio-bis(2-tertiary-butyl-5-methylphenol)) phenyl phosphite, bis(4,4'-n-butylidene-bis(2-tertiary-butyl-5-methylphenol)) phosphite, mono(4,4'-benzylidene-bis(2-tertiary-butyl-5-methylphenol)) phosphite, mono(2,2'-bis-(parahydroxyphenyl)propane)phosphite, mono(4,4'-butylidene-bis(2-tertiary-butyl-5-methylphenol)phosphite, bis(4,4'-thio-bis(2-tertiary-butyl-5-methylphenol)) phosphite, mono-2-ethylhexyl-mono-2,2'-methylene-bis(4-methyl-6,1'-methylcyclohexyl)-phenol phosphite, bis(2,2'-bis(para-hydroxyphenyl)-propane)phosphite, monoisooctylmono(4,4'-thio-bis(2-tertiary-butyl-5-methylphenol)) phosphite, isooctyl-(2,6-bis(2'-hydroxy-3,5-dinonylbenzyl)-4-nonylphenyl)) phosphite, tri-tridecyl-4,4'-n-butylidene-bis(2-tertiary-butyl-5-methylphenyl)diphosphite, triisooctyl-4,4'-thiobis(2-tertiary-butyl-5-methylphenyl)diphosphite, bis(2,2'-methylene-bis(4-methyl-6,1'-methyl cyclohexyl phenyl)) phosphite, isooctyl-4,4'-isopropylidene-bisphenyl phosphite, monophenyl mono(2,2'-methylene-bis(4-methyl-6,1'-methyl-cyclohexyl)) triphosphite, di-tridecyl-4,4'-oxydiphenyl diphosphite, di-n-dodecyl-4,4'-n-butylidene-bis(2-tertiary-butyl-5-methylphenyl)-diphosphite, di-tridecyl-4,4'-isopropylidene bisphenyl diphosphite, tetra-tridecyl butane-1,1,3-tris(2'-methyl-5-tertiary-butylphenyl-4)-triphosphite.

The thiodipropionic acid ester has the following formula:

$$R_1OOCCH_2CH_2-S-CH_2CH_2COOY$$

in which $R_1$ is an organic radical selected from the group consisting of hydrocarbon radicals such as alkyl, alkenyl, aryl, cycloalkyl and mixed alkyl aryl and mixed alkyl cycloalkyl radicals; hydroxyalkyl and hydroxyalkyloxyalkylene radicals; and esters thereof with aliphatic carboxylic acids; and Y is selected from the group consisting of (a) hydrogen, (b) a second R radical $R_2$, which can be the same as or different from the $R_1$ radical, (c) a polymeric chain of n thiodipropionic acid ester units:

$$-XO[OCCH_2CH_2SCH_2CH_2COOXO]_nOCCH_2CH_2-S-CH_2CH_2COOZ$$

where Z is hydrogen, $R_2$ or M, n is the number of thiodipropionic acid ester units in the chain, and X is a bivalent hydrocarbon group of the type of $R_1$, that is, alkylene, alkenylene, cycloalkylene, mixed alkylenearylene and mixed alkylenecycloalkylene radicals; hydroxyalkylene and hydroxyalkyloxyalkylene radicals; and esters thereof with aliphatic carboxylic acids; the value of n can range upwards from 0, but there is no upper limit on n except as is governed by the ratio of carbon atoms to sulfur atoms as stated below; and (d) a polyvalent metal M of Group II of the periodic table such as zinc, calcium, cadmium, barium, magnesium and strontium.

The molecular weights of the R and Y radicals are taken such that with the remainder of the molecule the thiodipropionic ester has a total of from about ten to about sixty carbon atoms per sulfur atom.

Accordingly, the various thiodipropionic acid ester species coming within the above-designated categories within the general formula can be defined as follows:
  (a) $R_1OOCCH_2CH_2SCH_2CH_2COOH$
  (b) $R_1OOCCH_2CH_2SCH_2CH_2COOR_2$
  (c) $R_1O[OCCH_2CH_2SCH_2CH_2COOX-O]_nOCCH_2CH_2SCH_2CH_2COOZ$
  (d) $R_1OOCCH_2CH_2SCH_2CH_2COOM$ In the above formulae $R_1$ and $R_2$, M, X and Z are the same as before and the value of $n_1$ can range upwards from 1, but there is no upper limit on $n_1$ except as is imposed by the ratio of carbon atoms, as stated below. In the polymer (c), as in the other forms of thiodipropionic acid esters, the total number of carbon atoms per sulfur atom is within the range from about ten to about sixty.

The R radical of these esters is important in furnishing compatibility with the polymer. The Y radical is desirably a different radical, $R_2$ or M or a polymer, where R is rather low in molecular weight, so as to compensate for this in obtaining the optimum compatibility and nonvolatility. Where Y is a metal, the thiodipropionic acid ester furnishes the beneficial properties of the polyvalent metal salt which is described above.

The aryl, alkyl, alkenyl, and cycloalkyl groups may, if desired, contain inert, nonreactive substituents such as halogen and other carbocyclic and heterocyclic ring structures condensed therewith.

Typical R radicals are, for example, methyl, ethyl, propyl, isopropyl, butyl, isobutyl, t-butyl, amyl, isoamyl, n-octyl, isooctyl, 2-ethyl hexyl, t-octyl, decyl, dodecyl, octadecyl, allyl, hexenyl, linoleyl, ricinoleyl, oleyl, phenyl, xylyl, tolyl, ethylphenyl, naphthyl, cyclohexyl, benzyl, cyclopentyl, methylcyclohexyl, ethylcyclohexyl, and naphthenyl, hydroxyethyl, hydroxypropyl, glyceryl, sorbityl, pentaerythrityl, and polyoxyalkylene radicals such as those derived from diethylene glycol, triethylene glycol, polyoxypropylene glycol, polyoxyethylene glycol, and polyoxypropyleneoxyethylene glycol, and esters thereof with any of the organic acids named below in the discussion of the polyvalent metal salts, including in addition those organic acids having from two to five carbon atoms, such as acetic, propionic, butyric and valeric acids.

Typical X radicals are alkylene radicals such as ethylene, tetramethylene, hexamethylene, decamethylene, alkyl-substituted alkylene radicals such as 1,2-propylene,

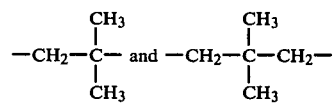

arylene radicals such as phenylene

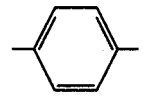

methylenephenylene

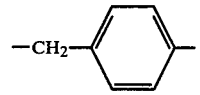

dimethylene phenylene

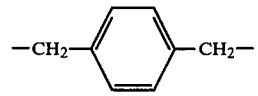

and alicyclylene such as cyclohexylene

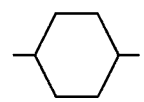

and cyclopentylene

As exemplary of the thiodipropionic acid esters which can be used, there can be mentioned the following: monolauryl thiodipropionic acid, dilauryl thiodipropionate, butyl stearyl thiodipropionate, 2-ethylhexyl lauryl thiodipropionate, di-2-ethylhexyl-thiodipropionate, diisodecyl thiodipropionate, isodecyl phenyl thiodipropionate, benzyl lauryl thiodipropionate, benzyl phenyl thiodipropionate, the diester of mixed coconut fatty alcohols and thiodipropionic acid, the diester of mixed tallow fatty alcohols and thiodipropionic acid, the acid ester of mixed cottonseed oil fatty alcohols and thiodipropionic acid, the acid ester of mixed soyabean oil fatty alcohols and thiodipropionic acid, cyclohexyl nonyl thiodipropionate, monooleyl thiodipropionic acid, hydroxyethyl lauryl thiodipropionate, monoglyceryl thiodipropionic acid, glyceryl monostearate monothiodipropionate, sorbityl isodecyl thiodipropionate, the polyester of diethylene glycol and thiodipropionic acid, the polyester of triethylene glycol and thiodipropionic acid, the polyester of hexamethylene glycol and thiodipropionic acid, the polyester of pentaerythritol and thiodipropionic acid, the polyester of octamethylene glycol and thiodipropionic acid, the polyester of p-dibenzyl alcohol and thiodipropionic acid, ethylbenzyl lauryl thiodipropionate, strontium stearyl thiodipropionate, magnesium oleyl thiodipropionate, calcium dodecylbenzyl thiodipropionate, and mono(dodecylbenzyl)thiodipropionic acid.

These esters are for the most part known compounds, but where they are not available, they are readily prepared by esterification of thiodipropionic acid and the corresponding alcohol.

Also useful are:

(1) Thioalkanoic acid amides of Tokuno et al Japanese Pat. No. 16,286/68 having the formula:

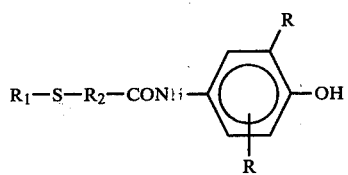

R is alkyl of one to eight carbon atoms, $R_1$ is alkyl of six to twenty-four carbon atoms, and $R_2$ is alkylene of one to six carbon atoms.

(2) Thioalkanoic acid amides of 1,3,5-triazines of Ozeki et al Japanese Pat. No. 20,366/68 having the formula:

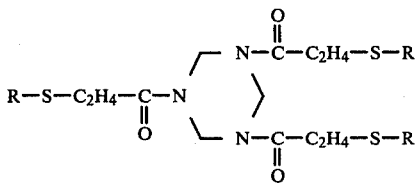

R is alkyl of eight to eighteen carbon atoms.

(3) Bis-thioalkanoic acid amides of Yamamoto et al Japanese Pat. No. 23,765/68 having the formula:

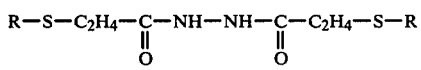

R is alkyl of more than six carbon atoms, aryl or aralkyl.

(4) Bis-thioalkylanoic acid amides of Ozeki et al Japanese Pat. No. 26,184/69 having the formula:

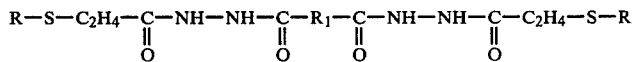

R is alkyl of twelve to eighteen carbon atoms, and $R_1$ is alkylene of one to ten carbon atoms, cycloalkylene, or arylene.

(5) Bis-alkylene thioalkanoic acid amides of Ozeki Japanese Pat. No. 31,464/69 having the formula:

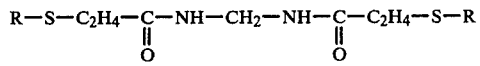

R is alkyl of more than six carbon atoms, aryl, or aralkyl.

(6) Thioalkanoic acid amide derivatives of Minagawa et al, published Japanese application No. 106,484/74 having the formula:

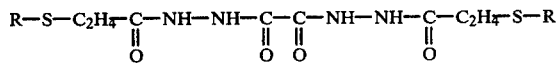

R is hydrocarbyl of one to twenty carbon atoms.

(7) Alkylene bis-thioalkanoic acid amides of U.S. Pat. No. 4,279,805 to Ohzeki et al, patented July 21, 1981, having the general formula:

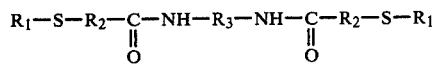

wherein:
$R_1$ is alkyl having from one to about fifty carbon atoms;
$R_2$ is alkylene having from one to about three carbon atoms; and
$R_3$ is alkylene having from about two to about twelve carbon atoms.

β-Alkylthiopropionic acid esters having the general formula:

wherein:

R is alkyl of four to twenty carbon atoms;
n is a number from 1 to 6; and
R' is the residue of an alcohol having from one to six hydroxyl groups.

Pentaerythritol tetra dodecyl thio propionate is an example of this group.

Other conventional light stabilizers can be employed, such as hydroxybenzophenones such as 2-hydroxy-4-methoxybenzophenone, 2-hydroxy-4-n-octoxybenzophenone, 2,4-dihydroxybenzophenone, benzotriazoles, such as 2(2-hydroxy-5-methylphenyl)benzotriazoles, 2(2-hydroxy-3-t-butyl-5-methylphenyl)-5-chlorobenzotriazole, 2(2-hydroxy-3-5-di-t-butylphenyl)5-chlorobenzotriazole, 2(2-hydroxy-3,5-di-t-amylphenyl)benzotriazole, benzoates such as phenylsalicylate, 2,4-di-t-butylphenyl-3,5-di-t-butyl-4-hydroxy phenylbenzoate, nickel compounds such as nickel-2,2'-thiobis(4-t-ocytl-phenolate), nickel-monoethyl(3,5-di-t-butyl-4-hydroxybenzyl)phosphonate, substituted acrylonitriles such as methyl-$\alpha$-cyano-$\beta$-methyl-$\beta$-(p-methoxyphenyl)acrylate and oxalic anilides such as N-2-ethyl phenyl-N'-2-ethoxy-5-t-butyl phenyl oxalic diamide, N-2-ethyl phenyl-N'-2-ethoxy phenyl oxalic diamide.

A sufficient amount of the stabilizer or combination is used to improve the resistance of the synthetic polymer to deterioration in physical properties when exposed to heat and light, including, for example, discoloration, reduction in melt viscosity and embrittlement. Very small amounts are usually adequate. Amounts within the range from about 0.001 to about 10% total stabilizers including the polyether piperidyl ester or ether by weight of the polymer are satisfactory. Preferably, from 0.01 to 5% is employed for optimum stablization.

The stabilizer systems of the invention are readily rendered in solid particulate form, comprising a blend of:
(a) polyether piperidyl ester or ether light stabilizer in an amount of from about 10 to about 35 parts by weight; and optionally:
(b) a phenolic antioxidant in an amount from about 10 to about 35 parts by weight; and/or
(c) other heat or light stabilizers in an amount of from about 10 to about 35 parts by weight.

The polyether piperidyl ester or ether of the invention can be employed in combination with phenolic antioxidant and/or other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organotin compounds; and epoxy compounds; and organic phosphites.

With polyolefin resins there can be employed fatty acid salts of polyvalent metals, and the higher fatty acid esters of thiodipropionic acids, such as, for example, dilauryl thiodipropionate.

With polyamide resin compositions, polyamide stabilizers such as copper salts in combination with iodides and/or other phosphorus compounds and salts of divalent manganese can be used.

With synthetic rubbers and acrylonitrile-butadienestyrene terpolymers, other antioxidants and polyvalent metal salts of the higher fatty acids can be used.

In addition, other conventional additives for synthetic polymers, such as plasticizers, lubricants, emulsifiers, anti-static agents, flame-proofing agents, pigments and fillers, can be employed.

The stabilizer or combination is incorporated in the polymer in suitable mixing equipment, such as a mill or a Banbury mixer. If the polymer has a melt viscosity which is too high for the desired use, the polymer can be worked until its melt viscosity has been reduced to the desired range before addition of the stabilizer. Mixing is continued until the mixture is substantially uniform. The resulting composition is then removed from the mixing equipment and brought to the size and shape desired for marketing or use.

The stabilized polymer can be worked into the desired shape, such as by milling, calendering, extruding or injection molding or fiber-forming. In such operations, it will be found to have a considerably improved resistance to reduction in melt viscosity during the heating, as well as a better resistance to discoloration and embrittlement or ageing and heating.

EXAMPLES 1 TO 8

Polypropylene compositions were prepared using stabilizers of the invention and three of the prior art, and having the following formulation:

| Ingredient | Parts by Weight |
| --- | --- |
| Polypropylene | 100 |
| Stearyl $\beta$-3,5-di-tert-butyl-4-hydroxyphenyl propionate | 0.2 |
| Stabilizer as shown in Table I | 0.3 |

The compositions were thoroughly blended in a Brabender Plastograph, and then compression-molded to form sheets 0.3 mm thick. Pieces 2.5 cm² were cut off from the sheets and exposed to a high voltage mercury lamp. Other 2.5 cm² pieces were immersed in hot water at 80° C. for 15 hours, and then exposed to the high voltage mercury lamp. The hours to failure were noted, and are shown in Table I.

TABLE I

| | | Hours to Failure | |
| --- | --- | --- | --- |
| Example No. | Stabilizer | Without immersion | After immersion for 15 hours |
| Control 1 | 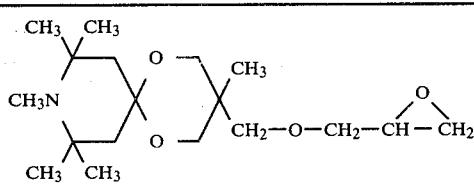 | 450 | 330 |

TABLE I-continued

| Example No. | Stabilizer | Hours to Failure Without immersion | Hours to Failure After immersion for 15 hours |
|---|---|---|---|
| Control 2 | [2,2,6,6-tetramethyl-1-methyl-4-piperidyl]-COO-CH$_2$-CH(-O-)CH$_2$ (glycidyl ester structure) | 480 | 370 |
| Control 3 | Polymer of 1-acetyl-2,2,6,6-tetramethyl-4-piperidyl glycidyl ether (M.W. = 1,600) | 560 | 490 |
| Example 1 | [1-methyl-2,2,6,6-tetramethyl-4-piperidyl spiro-ketal with C$_2$H$_5$/CH$_2$O-/CH$_2$-O- diol, -CH-CH$_2$O- linker]$_5$ | 880 | 850 |
| Example 2 | [1-oxyl-2,2,6,6-tetramethyl-4-piperidyl spiro-ketal with C$_2$H$_5$/CH$_2$O-/CH$_2$-O- diol, -CH-CH$_2$O- linker]$_4$ | 850 | 820 |
| Example 3 | [1-methyl-2,2,6,6-tetramethyl-4-piperidyl spiro-ketal with CH$_3$/CH$_2$O-/CH$_2$-O- diol, -CH-CH$_2$O- linker]$_8$ | 880 | 840 |
| Example 4 | [1-methyl-2,2,6,6-tetramethyl-4-piperidyl-CO-O-CH$_2$-CH(CH$_2$)-CH$_2$O-]$_{11}$ | 820 | 790 |
| Example 5 | [2,2,6,6-tetramethyl-4-piperidyl (NH)-CH$_2$CO-O-CH$_2$-CH(CH$_2$)-CH$_2$O-]$_7$ | 730 | 680 |
| Example 6 | [2,2,6,6-tetramethyl-4-piperidyl (NH) spiro-ketal with CH$_3$/CO-O/CH$_2$-O- diol, -CH-CH$_2$O- linker]$_5$ | 770 | 730 |

TABLE I-continued

| Example No. | Stabilizer | Hours to Failure Without immersion | Hours to Failure After immersion for 15 hours |
|---|---|---|---|
| Example 7 | [Structure: 1-oxyl-2,2,6,6-tetramethylpiperidine with spiro dioxane bearing -CO-O-CH$_2$-CH(CH$_2$-)-CH$_2$O- repeat unit]$_6$ (CH$_3$ substituent on central C) | 750 | 720 |
| Example 8 | [Structure: 1-methyl-2,2,6,6-tetramethylpiperidine with spiro dioxane bearing -CO-O-CH$_2$-CH(CH$_2$-)-CH$_2$O- repeat unit]$_9$ | 770 | 720 |

The superiority of the polyethers of the invention as compared to the prior art compounds is apparent from the data.

EXAMPLES 9 TO 18

Conventional stabilizers for polymeric materials may lose their effectiveness because of volatilization or decomposition at high polymer processing temperatures. This is not true of the stabilizers of the invention, as shown by observing the effect of heat in repeated extrusions of ethylenepropylene copolymer compositions. These compositions were prepared using stabilizers of the invention and of the prior art, and having the following formulation:

| Ingredient | Parts by Weight |
|---|---|
| Ethylene-propylene copolymer | 100 |
| Ca stearate | 0.2 |
| Stearyl-(3,5-di-t-butyl-4-hydroxyphenyl) propionate | 0.1 |
| Dilauryl thiodipropionate | 0.2 |
| Stabilizer as shown in Table II | 0.2 |

The ingredients were mixed and the compositions then extruded (cylinder temperature 230° C. and 240° C., head die temperature 250° C., velocity 20 rpm) five times. Test pieces were then molded by injection molding at 250° C. The test pieces were exposed to a high voltage mercury lamp, and the hours to failure were noted. The results are shown in Table II.

TABLE II

| Example No. | Stabilizer | Hours to Failure Extruded once | Hours to Failure Extruded 5 times |
|---|---|---|---|
| Control 1 | [1-methyl-2,2,6,6-tetramethylpiperidine-4-spiro-dioxane with C$_2$H$_5$ substituent, -CH$_2$-O-CH$_2$-CH(-O-)CH$_2$ glycidyl group] | 420 | 280 |
| Control 2 | [1-methyl-2,2,6,6-tetramethylpiperidin-4-yl -COO-CH$_2$-CH(-O-)CH$_2$ glycidyl ester] | 390 | 240 |
| Control 3 | Polymer of 1-acetyl-2,2,6,6-tetramethyl-4-piperidyl glycidyl ether (M.W. = 1,600) | 510 | 340 |
| Example 9 | [1-methyl-2,2,6,6-tetramethylpiperidine-4-spiro-dioxane with C$_2$H$_5$ and -CH$_2$-O- bridge, bearing -CH-CH$_2$O- / CH$_2$ / CH$_2$-O repeat unit]$_5$ | 660 | 620 |

TABLE II-continued
| Example No. | Stabilizer | Hours to Failure Extruded once | Extruded 5 times |
|---|---|---|---|
| Example 10 | 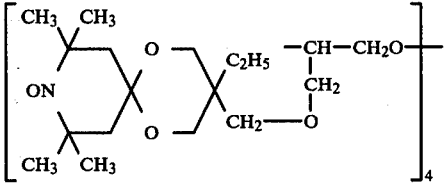 | 630 | 580 |
| Example 11 | 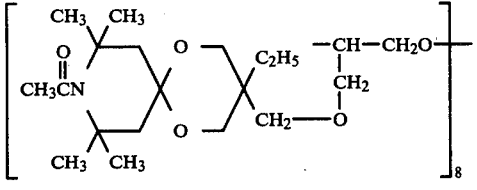 | 620 | 580 |
| Example 12 | 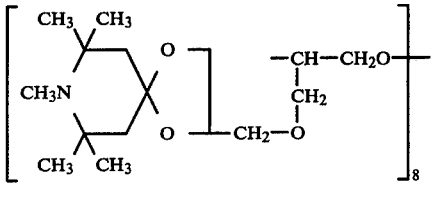 | 640 | 590 |
| Example 13 | 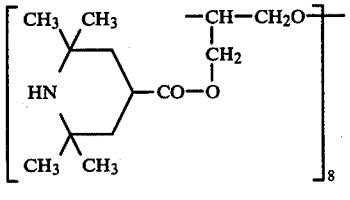 | 630 | 570 |
| Example 14 | 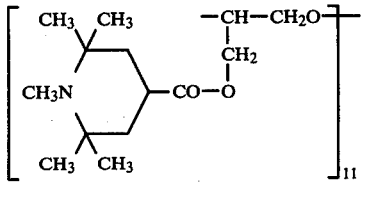 | 630 | 590 |
| Example 15 | 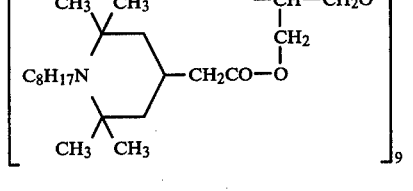 | 590 | 530 |
| Example 16 | 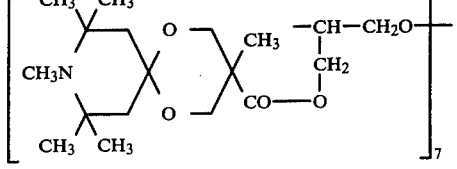 | 650 | 600 |

TABLE II-continued

| Example No. | Stabilizer | Hours to Failure | |
|---|---|---|---|
| | | Extruded once | Extruded 5 times |
| Example 17 | [structure: 2,2,6,6-tetramethyl-piperidine with HN, linked via O—CO—O to —CH—CH₂O— with CH₂ branch]₅ | 620 | 570 |
| Example 18 | [structure: 1-acetyl-2,2,6,6-tetramethyl-piperidine (CH₃CN with =O) linked via O—CO—O to —CH—CH₂O— with CH₂ branch]₁₃ | 600 | 540 |

The superiority of the polyethers of the invention as compared to the prior art compounds is apparent from the data.

EXAMPLES 19 TO 27

High density polyethylene compositions were prepared using stabilizers of the invention and three of the prior art, and having the following formulation:

| Ingredient | Parts by Weight |
|---|---|
| High-density polyethylene | 100 |
| Ca stearate | 1 |
| Tetrakis-(methylene-3-(3,5-di-t-butyl-4-hydroxyphenyl) propionate) | 0.1 |

| Ingredient | Parts by Weight |
|---|---|
| methane | |
| Distearylthiodipropionate | 0.3 |
| Stabilizer as shown in Table III | 0.2 |

The stabilizer was blended with the polymer on a two-roll mill, and sheets 0.5 mm thick were prepared by compression-molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and the results are reported in Table III.

TABLE III

| Example No. | Stabilizer | Hours to Failure |
|---|---|---|
| Control 1 | [1-methyl-2,2,6,6-tetramethylpiperidine (CH₃N) linked via O—O to C(CH₃)₂—CH₂—O—CH₂—CH—CH₂ epoxide] | 780 |
| Control 2 | [1-methyl-2,2,6,6-tetramethylpiperidine (CH₃N) —COO—CH₂—CH—CH₂ epoxide] | 750 |
| Control 3 | Polymer of 1-acetyl-2,2,6,6-tetramethyl-4-piperidyl glycidyl ether (M.W. = 1,600) | 860 |
| Example 19 | [1-methyl-2,2,6,6-tetramethylpiperidine (CH₃N) linked via O—O to C(C₂H₅)(CH₂—O)— with —CH—CH₂O— and CH₂ branch]₅ | 1,250 |

TABLE III-continued

| Example No. | Stabilizer | Hours to Failure |
|---|---|---|
| Example 20 | [structure with CH₃CON-piperidine spiro dioxane, C₂H₅, -CH-CH₂O-]₈ | 1,170 |
| Example 21 | [structure with CH₃N-piperidine spiro dioxane, CH₃, -CH-CH₂O-]₈ | 1,250 |
| Example 22 | [structure with HN-piperidine, OH, CO-O, -CH-CH₂O-]₈ | 1,090 |
| Example 23 | [structure with CH₃N-piperidine, CO-O, -CH-CH₂O-]₁₁ | 1,220 |
| Example 24 | [structure with C₈H₁₇N-piperidine, CH₂CO-O, -CH-CH₂O-]₉ | 1,140 |
| Example 25 | [structure with HN-piperidine spiro dioxane, CH₃, CO-O, -CH-CH₂O-]₅ | 1,200 |
| Example 26 | [structure with ON-piperidine spiro dioxane, CH₃, CO-O, -CH-CH₂O-]₆ | 1,050 |

TABLE III-continued

| Example No. | Stabilizer | Hours to Failure |
|---|---|---|
| Example 27 | $\left[\begin{array}{c}\text{2,2,6,6-tetramethylpiperidyl ring with HN, connected via O-CO-O to -CH(CH}_2\text{-O-)-CH}_2\text{-O- cyclic acetal}\end{array}\right]_5$ | 1,160 |

The superiority of the polyethers of the invention as compared to the prior art compounds is apparent from the data.

EXAMPLES 28 TO 35

Ethylene-vinyl acetate copolymer compositions were prepared using stabilizers of the invention and three of the prior art, and having the following formulation:

| Ingredient | Parts by Weight |
|---|---|
| Ethylene-vinylacetate copolymer | 100 |
| Stearyl-3,5-di-t-butyl-4-hydroxy phenylpropionate | 0.05 |
| Ca stearate | 0.1 |
| Zn stearate | 0.1 |
| Diisodecylphenylphosphite | 0.2 |
| Stabilizer as shown in Table IV | 0.2 |

The stabilizer was blended with the polymer on a two-roll mill at 130° C., and sheets 0.4 mm thick were then compression-molded at 140° C. from the resulting blend. Pieces 2.5 cm square were cut off from the sheets and exposed to ultraviolet light in a Weather-O-Meter for 500 hours. At the start and at the conclusion of the test, tensile strength of the sheet samples was determined. The results are shown in Table IV as % retention of the initially determined tensile strength.

TABLE IV

| Example No. | Stabilizer | % Retention of Tensile Strength After 500 Hours |
|---|---|---|
| Control 1 | 1,2,2,6,6-pentamethylpiperidyl structure with -CH$_2$-O-CH$_2$-CH(epoxide)CH$_2$ substituent | 63 |
| Control 2 | 1,2,2,6,6-pentamethylpiperidyl structure with -COO-CH$_2$-CH(epoxide)CH$_2$ substituent | 65 |
| Control 3 | Polymer of 1-acetyl-2,2,6,6-tetramethyl-4-piperidyl glycidyl ether (M.W. = 1,600) | 66 |
| Example 28 | $\left[\text{1,2,2,6,6-pentamethylpiperidyl-spiro-dioxane with C}_2\text{H}_5\text{ and -CH(CH}_2\text{O-)-CH}_2\text{-O-}\right]_5$ | 83 |
| Example 29 | $\left[\text{1,2,2,6,6-pentamethylpiperidyl-spiro-dioxane with CH}_3\text{ and -CH(CH}_2\text{O-)-CH}_2\text{-O-}\right]_8$ | 83 |

TABLE IV-continued

| Example No. | Stabilizer | % Retention of Tensile Strength After 500 Hours |
|---|---|---|
| Example 30 | [structure: 2,2,6,6-tetramethyl-N-methyl-piperidine spiroketal with –CH–CH₂O– / CH₂ / CH₂–O– repeating unit]₈ | 78 |
| Example 31 | [structure: 2,2,6,6-tetramethylpiperidine (HN) with –CO–O– linkage to –CH–CH₂O– / CH₂ repeating unit]₈ | 80 |
| Example 32 | [structure: 2,2,6,6-tetramethylpiperidine (HN) with –CH₂CO–O– linkage to –CH–CH₂O– / CH₂ repeating unit]₇ | 78 |
| Example 33 | [structure: 2,2,6,6-tetramethyl-N-methyl-piperidine spiroketal with CH₃ and CO–O linkage to –CH–CH₂O– / CH₂ repeating unit]₇ | 81 |
| Example 34 | [structure: 2,2,6,6-tetramethylpiperidine (HN) spiroketal with CO–O linkage to –CH–CH₂O– / CH₂ repeating unit]₅ | 79 |
| Example 35 | [structure: 2,2,6,6-tetramethyl-N-methyl-piperidine spiroketal with CO–O linkage to –CH–CH₂O– / CH₂ repeating unit]₉ | 79 |

The superiority of the polyethers of the invention as compared to the prior art compounds is apparent from the data.

EXAMPLES 36 TO 42

Acrylonitrile-butadiene-styrene terpolymer resin compositions were prepared using stabilizers of the invention and three of the prior art, and having the following formulations:

| Ingredient | Parts by Weight |
|---|---|
| Acrylonitrile-butadiene-styrene terpolymer | 100 |
| 4,4'-butylidene-bis(2-tert-butyl-m-cresol) | 0.1 |
| Stabilizer as shown in Table V | 0.3 |

The stabilizer was blended with the resin on a two-roll mill, and sheets 3 mm thick were prepared by compression-molding of the resulting blend. Pieces 2.5 cm square were cut off from the sheets, and subjected to ultraviolet light in a Weather-O-Meter for 800 hours. Tensile strength before and after the test exposure was determined, and the results are reported as the percent of tensile strength retained at the end of this time, in Table V.

TABLE V

| Example No. | Stabilizer | % Tensile Strength Retained |
|---|---|---|
| Control 1 | [structure: 1,2,2,6,6-pentamethyl-4-piperidyl ketal with CH₂—O—CH₂—CH(—O—)CH₂ glycidyl ether] | 59 |
| Control 2 | [structure: 1,2,2,6,6-pentamethyl-4-piperidyl ketal with COO—CH₂—CH(—O—)CH₂ glycidyl ester] | 63 |
| Control 3 | Polymer of 1-acetyl-2,2,6,6-tetramethyl-4-piperidyl glycidyl ether (M.W. = 1,600) | 65 |
| Example 36 | [structure: 1,2,2,6,6-pentamethyl-4-piperidyl ketal with C₂H₅/CH₂/CH₂—O branched unit, repeating —CH—CH₂O—, n=5] | 85 |
| Example 37 | [structure: 1,2,2,6,6-pentamethyl-4-piperidyl ketal with CH₃/CH₂/CH₂—O branched unit, repeating —CH—CH₂O—, n=8] | 85 |
| Example 38 | [structure: 2,2,6,6-tetramethyl-4-piperidyl (OH, CO—O) unit, repeating —CH—CH₂O— with CH₂, n=8] | 79 |
| Example 39 | [structure: 2,2,6,6-tetramethyl-4-piperidyl —CO—O— unit, repeating —CH—CH₂O— with CH₂, n=8] | 83 |
| Example 40 | [structure: 1-octyl-2,2,6,6-tetramethyl-4-piperidyl —CH₂CO—O— unit, repeating —CH—CH₂O— with CH₂, n=9] | 80 |

TABLE V-continued

| Example No. | Stabilizer | % Tensile Strength Retained |
|---|---|---|
| Example 41 | [structure: 2,2,6,6-tetramethyl-1-methyl-piperidine with spiro dioxane linked to -CH-CH2O-/CH2/CO-O unit]₇ | 84 |
| Example 42 | [structure: 1-acetyl-2,2,6,6-tetramethylpiperidine with spiro dioxane linked to -CH-CH2O-/CH2/CO-O unit]₁₃ | 80 |

The superiority of the polyethers of the invention as compared to the prior art compounds is apparent from the data.

EXAMPLES 43 TO 50

A group of polyvinyl chloride resin compositions was prepared having the following formulation:

| Ingredient | Parts by Weight |
|---|---|
| Polyvinyl chloride | 100 |
| Dioctylphthalate | 48 |
| Epoxidized soybean oil | 2 |
| Tris nonyl phenyl phosphite | 0.2 |
| Ca stearate | 1.0 |
| Zn stearate | 0.1 |
| Stabilizer as shown in Table VI | 0.3 |

This formulation was blended and sheeted off on a two-roll mill to form sheets 1 mm thick. The light resistance of these sheets was then determined by placing strips 1 cm wide in a Weather-O-Meter, and exposing them to ultraviolet light. The time in hours was then noted for the sheets to develop a noticeable discoloration and/or embrittlement, indicating deterioration due to oxidation in the presence of ultraviolet light. The results obtained are shown in Table VI.

TABLE VI

| Example No. | Stabilizer | Hours to Failure |
|---|---|---|
| Control 1 | None | 210 |
| Control 2 | [structure: 1-methyl-2,2,6,6-tetramethylpiperidine spiro dioxane with CH2-O-CH2-CH-CH2 epoxide] | 370 |
| Control 3 | Polymer of 1-acetyl-2,2,6,6-tetramethyl-4-piperidyl glycidyl ether (M.W. = 1,600) | 430 |
| Example 43 | [structure: 1-oxyl-2,2,6,6-tetramethylpiperidine spiro dioxane with C2H5 and -CH-CH2O-/CH2/CH2-O unit]₄ | 820 |
| Example 44 | [structure: 1-acetyl-2,2,6,6-tetramethylpiperidine spiro dioxane with C2H5 and -CH-CH2O-/CH2/CH2-O unit]₈ | 790 |

TABLE VI-continued

| Example No. | Stabilizer | Hours to Failure |
|---|---|---|
| Example 45 | (structure) | 810 |
| Example 46 | (structure) | 770 |
| Example 47 | (structure) | 750 |
| Example 48 | (structure) | 800 |
| Example 49 | (structure) | 770 |
| Example 50 | (structure) | 790 |

The superiority of the polyethers of the invention as compared to the prior art compounds is apparent from the data.

EXAMPLES 51 TO 57

Polyurethane resin compositions were prepared using stabilizers of the invention and having the following formulation:

| Ingredient | Parts by Weight |
|---|---|
| Polyurethane resin (Asahi Denka[1] U-100) | 100 |
| Ba stearate | 0.7 |
| Zn stearate | 0.3 |
| 2,6-di-t-butyl-p-cresol | 0.1 |
| Stabilizer as shown in Table VII | 0.3 |

[1] A polyurethane-isocyanurate made from toluene diisocyanate and alkylene polyol.

The stabilizer was blended with the finely powdered polyurethane resin on a two-roll mill for five minutes at 70° C., and the sheet was then compression-molded at 120° C. for five minutes to form sheets 0.5 mm thick. Pieces 2.5 cm square were cut out from the sheets, and exposed to ultraviolet light in a Weather-O-Meter for thirty hours. Elongation before and after exposure was determined, and the percent elongation retained after the exposure is given in Table VII.

TABLE VII

| Example No. | Stabilizer | % Elongation Retention |
|---|---|---|
| Control 1 | [structure: 2,2,6,6-tetramethyl-1-methylpiperidine linked via spiro dioxane to CH₂—O—CH₂—CH(epoxide)CH₂] | 54 |
| Control 2 | Polymer of 1-acetyl-2,2,6,6-tetramethyl-4-piperidyl glycidyl ether (M.W. = 1,600) | 61 |
| Example 51 | [structure with C₂H₅ branch, repeat unit n=5] | 78 |
| Example 52 | [structure with CH₃ branch, repeat unit n=8] | 78 |
| Example 53 | [structure, repeat unit n=8] | 77 |
| Example 54 | [structure with CO—O linkage, repeat unit n=11] | 75 |
| Example 55 | [structure with C₈H₁₇N, CH₂CO—O linkage, repeat unit n=9] | 72 |
| Example 56 | [structure with HN, repeat unit n=5] | 77 |

TABLE VII-continued

| Example No. | Stabilizer | % Elongation Retention |
|---|---|---|
| Example 57 | 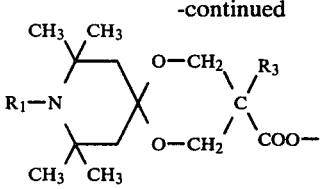 | 74 |

The superiority of the polyethers of the invention as compared to the prior art compounds is apparent from the data.

Having regard to the foregoing disclosure, the following is claimed as the inventive and patentable embodiments thereof:

1. Polyethers containing 2,2,6,6-tetramethyl piperidinyl carboxylic acid ester or ether groups comprising polymeric units having the structure

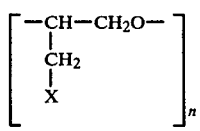    I wherein
X is selected from the group consisting of:

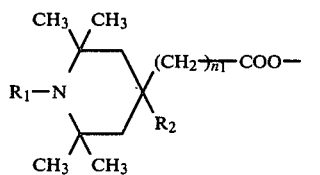

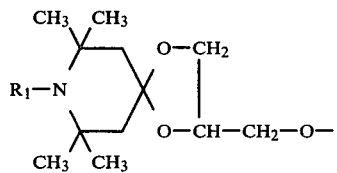

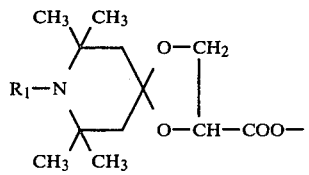

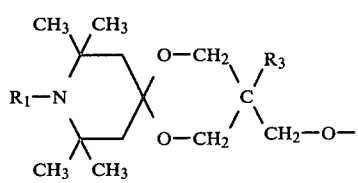

-continued

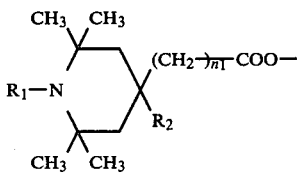

$R_1$ is selected from the group consisting of hydrogen, —O, alkyl, hydroxy alkyl and epoxyalkyl having from one to about eighteen carbon atoms, acyl having from one to about eighteen carbon atoms, cycloalkyl having from three to about eighteen carbon atoms; phenyl; phenalkyl and alkylphenyl having from seven to about twenty-four carbon atoms;

$R_2$ is hydrogen or hydroxy;

$n_1$ is 0 or 1;

$R_3$ is lower alkyl having from one to about six carbon atoms; and n is the average number of such units in the polyether, within the range from 2 to 50.

2. Polyethers according to claim 1 in which X has the formula

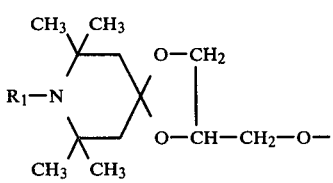

wherein $R_1$, $R_2$ and $n_1$ are as in claim 1.

3. Polyethers according to claim 1 in which X has the formula

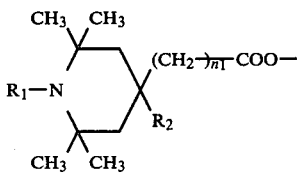

wherein $R_1$ is as claim 1.

4. Polyethers according to claim 1 in which X has the formula

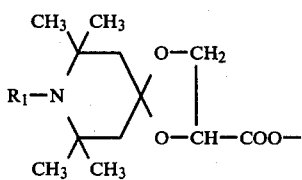

wherein R₁ is as in claim 1.

5. Polyethers according to claim 1 in which X has the formula

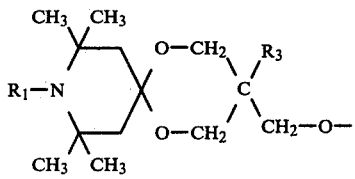

wherein R₁ and R₃ are as in claim 1.

6. Polyethers according to claim 1 in which X has the formula

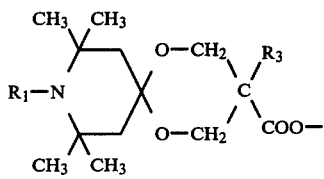

wherein R₁ and R₃ are as in claim 1.

7. Polyethers according to claim 1 wherein n is a number from 2 to 5.

8. Polyethers according to claim 1 wherein n is a number from 3 to 20.

9. Polyethers according to claim 1 wherein R₁ is hydrogen.

10. Polyethers according to claim 1 wherein R₁ and R₂ are each hydrogen.

11. Polyethers according to claim 1 having the formula:

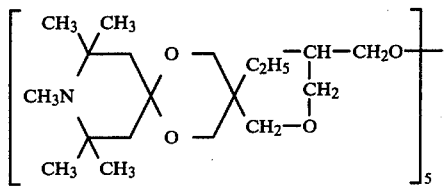

12. Polyethers according to claim 1 having the formula:

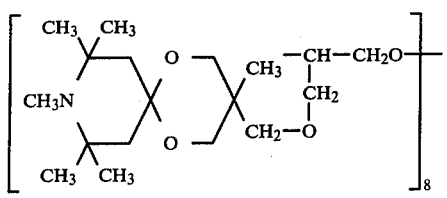

13. Polyethers according to claim 1 having the formula:

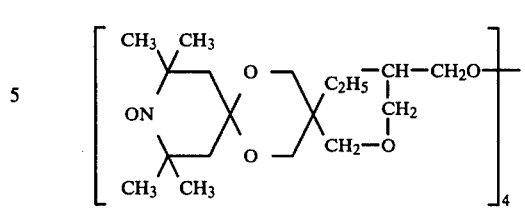

14. Polyethers according to claim 1 having the formula:

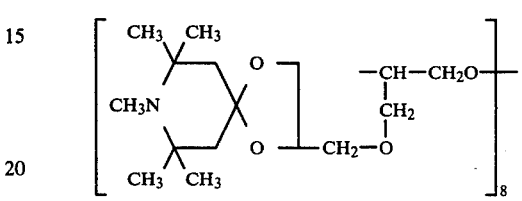

15. Polyethers according to claim 1 having the formula:

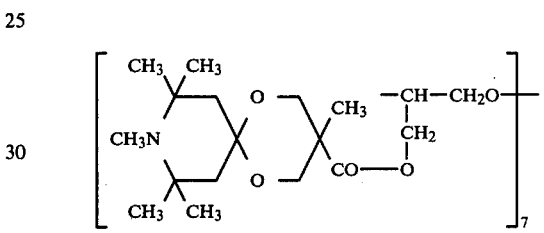

16. A polyvinyl chloride resin composition having improved resistance to deterioration upon exposure to light comprising a polyvinyl chloride resin formed at least in part of the recurring group:

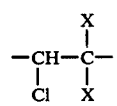

and having a chlorine content in excess of 40%, where X is either hydrogen or chlorine; and a compound in accordance with claim 1.

17. A polyvinyl chloride resin composition in accordance with claim 16 in which the polyvinyl chloride resin is polyvinyl chloride homopolymer.

18. A polyvinyl chloride resin composition in accordance with claim 16 in which the polyvinyl chloride resin is a copolymer of vinyl chloride and vinyl acetate.

19. An olefin polymer composition having improved resistance to deterioration upon exposure to light comprising an olefin polymer selected from the group consisting of polymers of alpha-olefins having from two to six carbon atoms and polystyrene, and a compound in accordance with claim 1.

20. An olefin polymer composition in accordance with claim 19 wherein the polyolefin is polypropylene.

21. An olefin polymer composition in accordance with claim 19 wherein the polyolefin is polyethylene.

22. An olefin polymer composition in accordance with claim 19 wherein the polyolefin is ethylene-propylene copolymer.

23. A polyurethane resin composition having improved resistance to deterioration upon exposure to light comprising a polyurethane resin and a compound in accordance with claim 1.

24. An ethylene-vinyl acetate copolymer composition having improved resistance to deterioration upon exposure to light comprising an ethylene-vinyl acetate copolymer and a compound in accordance with claim 1.

25. An acrylonitrile-butadiene-styrene copolymer composition having improved resistance to deterioration upon exposure to light comprising an acrylonitrile-butadiene-styrene copolymer and a compound in accordance with claim 1.

* * * * *